US011293919B2

(12) United States Patent
Shachar et al.

(10) Patent No.: US 11,293,919 B2
(45) Date of Patent: Apr. 5, 2022

(54) APPARATUS AND METHOD FOR OVERCOMING MINIMAL MASS SENSITIVITY LIMITATIONS IN A SHEAR HORIZONTAL SURFACE ACOUSTIC WAVE BIOSENSOR

(71) Applicant: Sensor Kinesis Corporation, Inglewood, CA (US)

(72) Inventors: Josh Shachar, Santa Monica, CA (US); Roger Kornberg, Atherton, CA (US)

(73) Assignee: Autonomous Medical Devices Inc., Santa Ana, CA (US)

( * ) Notice: Subject to any disclaimer, the term of this patent is extended or adjusted under 35 U.S.C. 154(b) by 363 days.

(21) Appl. No.: 16/714,421

(22) Filed: Dec. 13, 2019

(65) Prior Publication Data
US 2021/0181192 A1    Jun. 17, 2021

(51) Int. Cl.
*G01N 33/00*    (2006.01)
*G01N 33/543*    (2006.01)
(Continued)

(52) U.S. Cl.
CPC .. *G01N 33/54333* (2013.01); *B01L 3/502715* (2013.01); *G01N 33/491* (2013.01); *G01N 33/541* (2013.01); *G01N 33/5434* (2013.01); *B01L 2300/0636* (2013.01); *B01L 2400/0436* (2013.01); *B01L 2400/06* (2013.01);
(Continued)

(58) Field of Classification Search
CPC .......... G01N 33/54333; G01N 33/491; G01N 33/541; G01N 33/5434; G01N 2446/20; G01N 2446/90; G01N 2458/10; G01N 33/54366; B01L 3/502715; B01L 2300/0636; B01L 2400/0436;
(Continued)

(56) References Cited

U.S. PATENT DOCUMENTS

| 2006/0205061 A1* | 9/2006 | Roukes ................. B01L 3/5027 435/287.2 |
| 2008/0199930 A1* | 8/2008 | Lee ........................ C12M 47/06 435/306.1 |

(Continued)

FOREIGN PATENT DOCUMENTS

EP    1946841 A1 *    7/2008    ............ B01L 3/5027

*Primary Examiner* — Christopher L Chin
*Assistant Examiner* — Mohammad Ali Al-Ameen
(74) *Attorney, Agent, or Firm* — Marcus C. Dawes; Daniel L. Dawes

(57) ABSTRACT

The invention includes a method of assaying an analyte in a sample in a portable, handheld microfluidic reader. The method includes the steps of: inserting the sample in the reader; capturing the analyte with a first antibody having a DNA tag attached thereto; capturing the analyte in the sample with a second antibody attached to a surface or having a magnetic nanoparticle (MNP) attached thereto; where a sandwich including the magnetic nanoparticle, first and second antibodies, the analyte and the DNA tag is formed; replicating the DNA tag using isothermal amplification to a predetermined amount of DNA tags detectable by a detector sufficient to overcome the minimal mass sensitivity limitations of the detector; and measuring the amount of replicated DNA tags using the detector. The invention also includes an apparatus or handheld portable field microfluidic reader in which the method is performed.

20 Claims, 18 Drawing Sheets

(51) Int. Cl.
*G01N 33/541* (2006.01)
*G01N 33/49* (2006.01)
*B01L 3/00* (2006.01)

(52) U.S. Cl.
CPC ..... *G01N 2446/20* (2013.01); *G01N 2446/90* (2013.01); *G01N 2458/10* (2013.01)

(58) Field of Classification Search
CPC ............ B01L 2400/06; B01L 2200/16; B01L 2300/0803; B01L 2400/0409; B01L 3/50273
USPC ...... 310/313 R, 340; 436/45, 177, 526, 806; 435/6.12, 7.94, 91.1, 91.2, 30, 291.7; 422/415, 72, 506, 533, 548, 918; 73/7.82
See application file for complete search history.

(56) References Cited

U.S. PATENT DOCUMENTS

2009/0317896 A1* 12/2009 Yoo ..................... F16K 99/0057
 435/287.1
2018/0334697 A1* 11/2018 Shachar ............... C12Q 1/6825

* cited by examiner

1. Fast, Highly Controlled Amplification
2. DNA Sequence Is Customizable And Synthetic, Providing High Specificity For DNA Mass Amplification That Occurs If And Only If Troponin, DNA Primers, And Polymerase Enzyme Are Present.
3. Simplifies Sensor Functionalization.
4. DNA Is A Highly Stable And Easily Linked To Any Antibody, Making It A Universal Amplifier For The SAW.

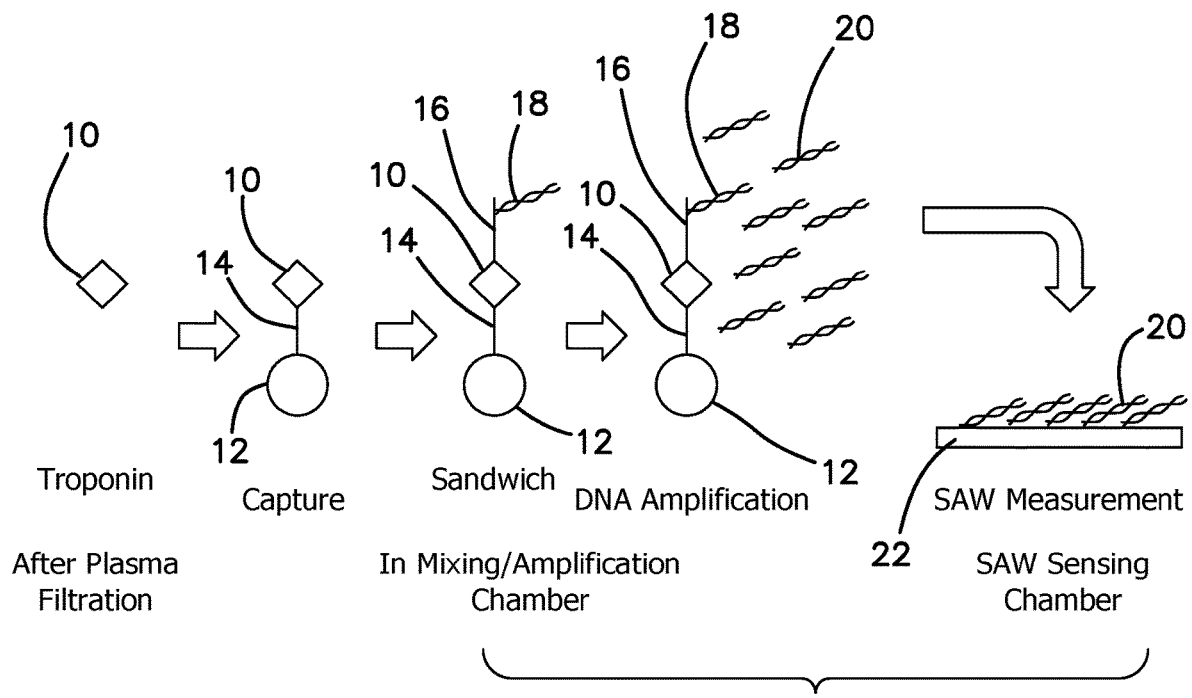

FIG. 1

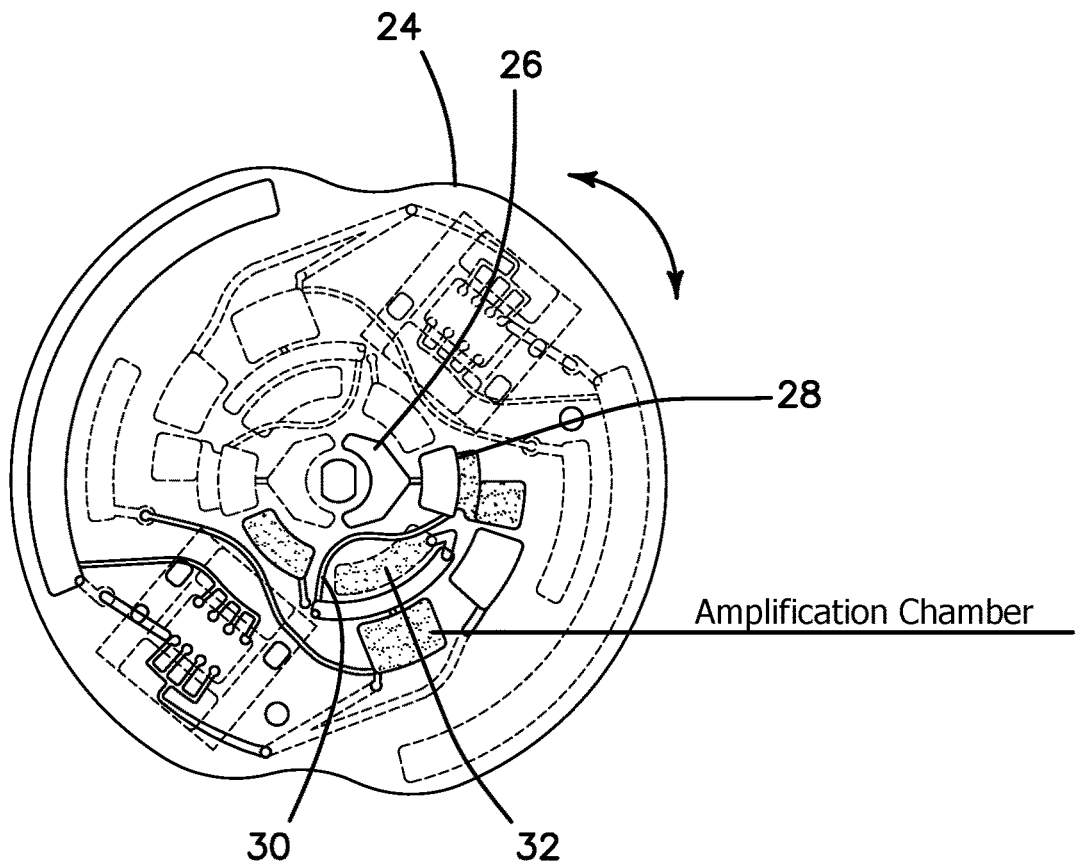
Amplification Chamber
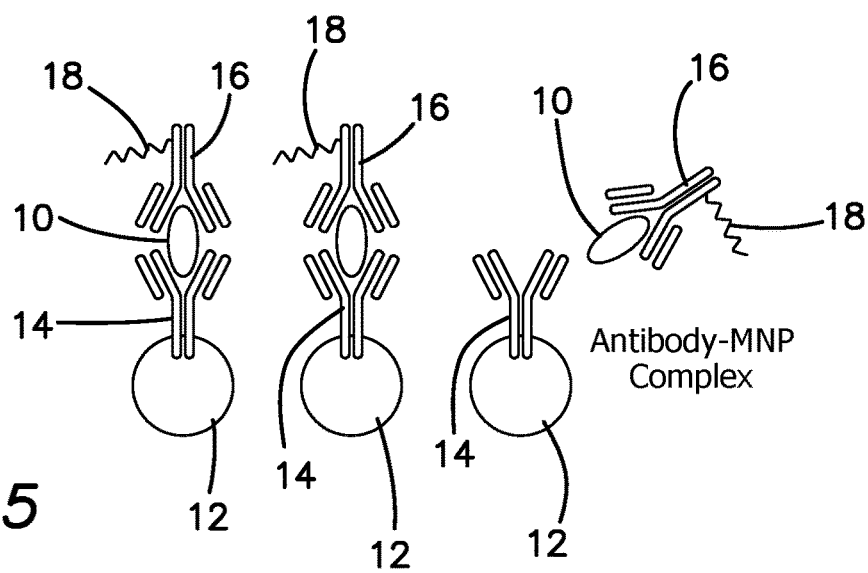
FIG. 5
Troponin-Antibody-DNA Complex Binds WIth Antibody-MNP Complex As Disc Is Oscillated Back And Forth FIG. 6      MNP Complexes Are Held In Place By A Magnet While Plasma And Other Contaminants Are Removed From The Chamber An Extra Wash Flushes The Chamber Ensuring Only Bound Troponin-DNA-MNP Complexes Are Left

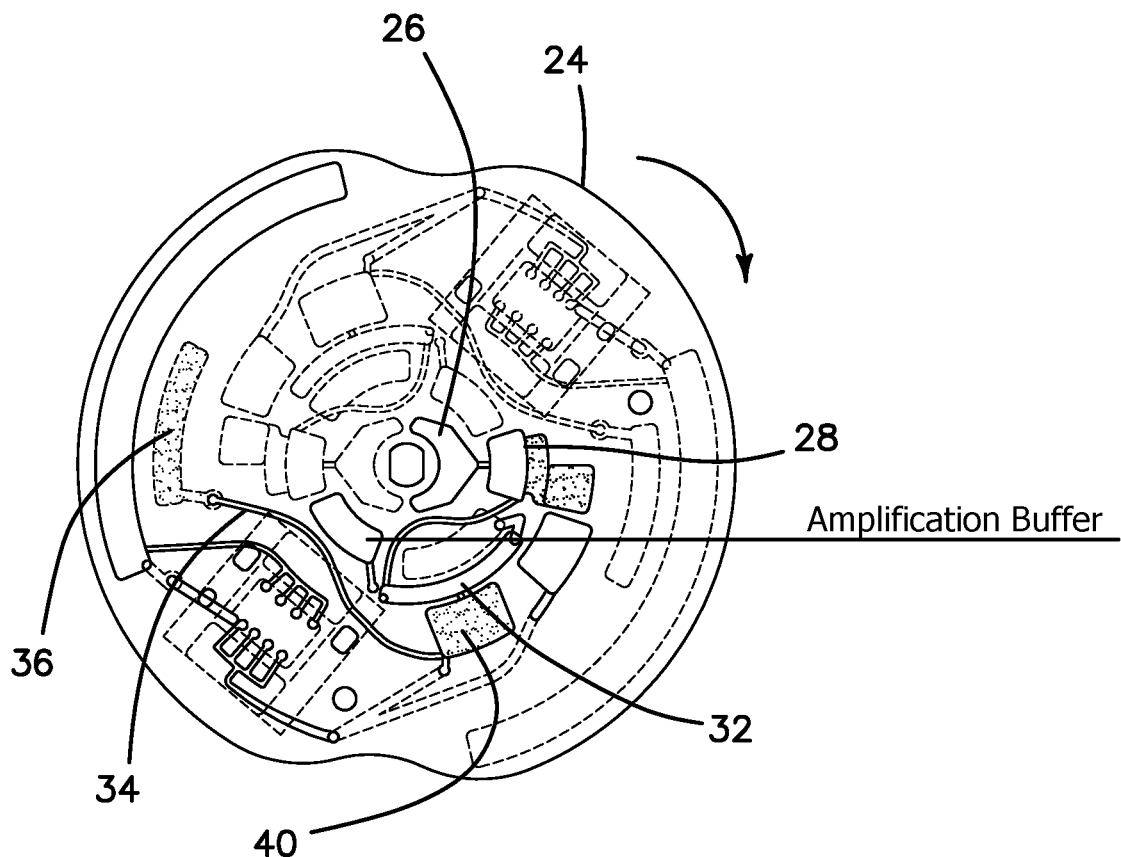
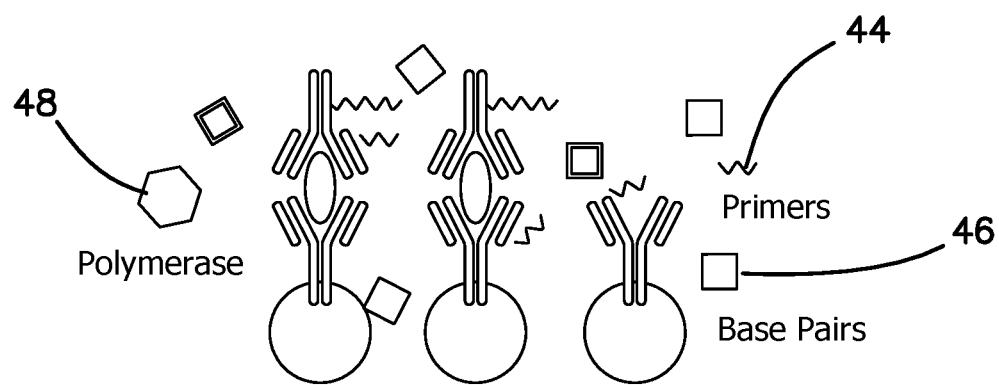
FIG. 8  A Buffer Containing Primers, Base Pairs, And Polymerase Is Used To Resuspend The Complexes In Order To Start The Amplification Reaction Amplified DNA Fragments 1. Peltier Element Holds Chamber At Proper Temperature (65 C)
2. Each DNA Fragment Is Amplified $10^9$ Times in ~10 Min The Amplified DNA Fragments Are Spun Down And Allowed To Settle On The SAW Sensor The Sensor Is Washed And Spun Dry To Remove Any Excess Contamination And Ensure The Signal Is Only From The Amplified DNA An RF Signal Is Send To The SAW Sensor And The Received Signal Is Correlated To A Concentration Of Troponin. The Info Is Sent To The Cloud For Futher Processing.

CONTINUED (1)

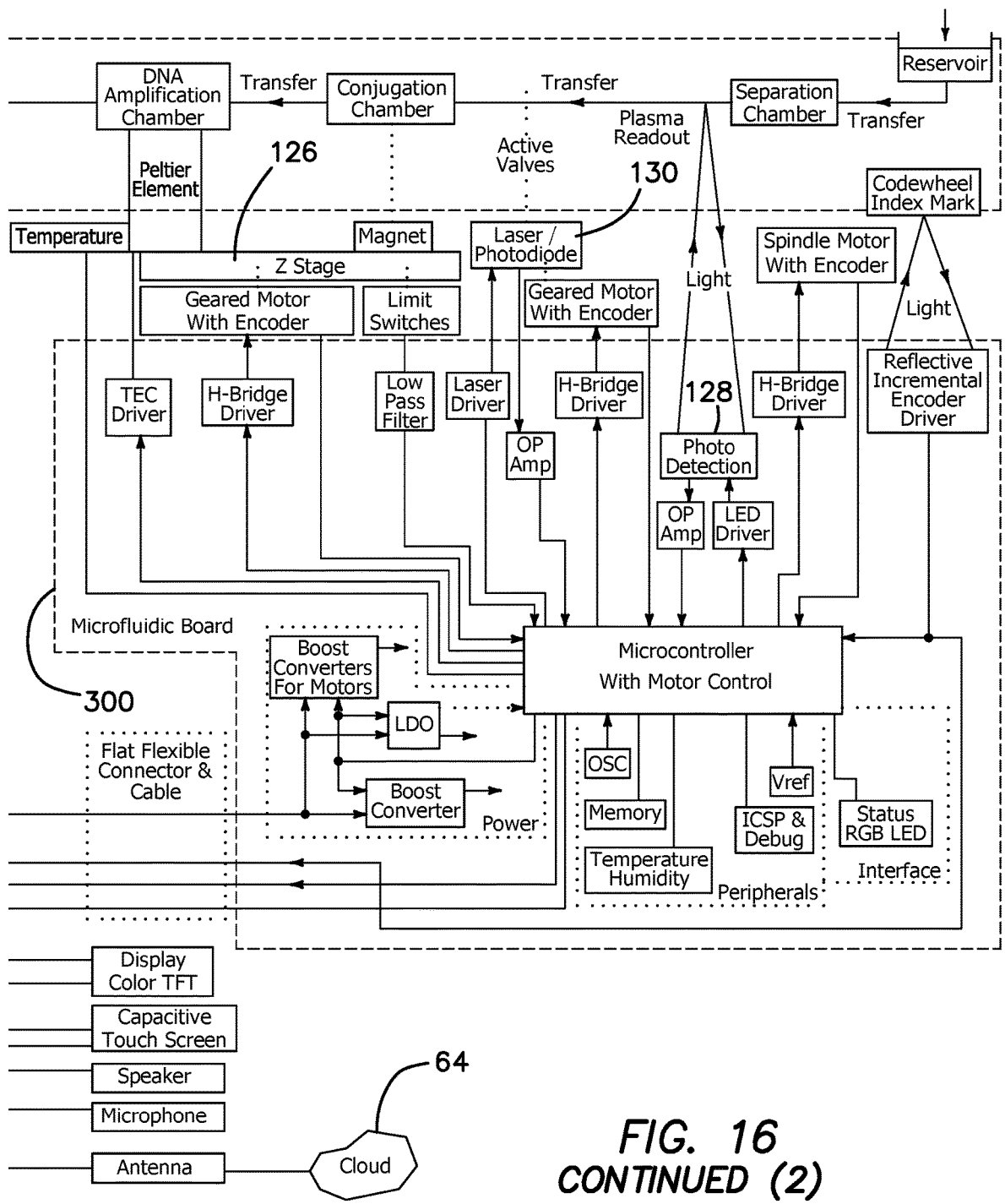
FIG. 16 CONTINUED (2)

APPARATUS AND METHOD FOR OVERCOMING MINIMAL MASS SENSITIVITY LIMITATIONS IN A SHEAR HORIZONTAL SURFACE ACOUSTIC WAVE BIOSENSOR

BACKGROUND

Field of the Technology

The invention relates to the field of detection of bioanalytes at ultra-low concentrations and in particular to a method for detecting biomarkers at concentration levels of less than 1000 femtograms/mL using a mass detector, such as a shear horizontal surface wave acoustic (SH SAW) detector.

Description of the Prior Art

Clinical measurement of bioanalytes at concentration levels in the range of pg/ml to ng/ml magnitudes is realized with current state of the art microfluidic devices employing a shear horizontal surface wave acoustic (SH SAW) detectors, such as provided in the Sensor Kinesis Optiku™ platform (Inglewood, Calif.). See U.S. Pat. Pub. 2019/0201900, incorporated herein by reference and hereinafter referred to as the "Incorporated Disclosure". To obtain its claimed sensitivities, the Optikus™ employs a mass enhanced SAW detection method using gold or magnetic particles attached to analyte capturing antigens. A wet-wet detection scheme and a wet-dry detection scheme is discussed in the Incorporated Disclosure. A sensitivity of 4-5 ng/ml in a wet-wet detection method, where the target is measured in liquid buffer on the SAW sensor, and a sensitivity of 12-24 pg/ml in a wet-dry detection method, where the liquid buffer is removed from the SAW sensor prior to detection, appears to be at or near the highest sensitivities to which the Optikus™ device can be pushed.

However, the standards of the Food and Drug Administration for the required sensitivity of a biomedical detector is that the detector be able to provide a sensed or detected output signal with a magnitude, which is at least three standard deviations above the lowest measurable signal above noise. In the case of the Optikus™ platform this means that in order to claim a sensitivity of 2 pg/ml the detector needs to be able to reliably measure concentrations at least as low as 800 fg/ml. This is two orders of magnitude lower than the minimum concentration which the Optikus™ appears to be capable of detecting, even using the best mass enhanced detection methodologies available.

Examples of successful implementation of the 36° YX lithium tantalate SH SAW device for detection of viral particles in a conjugation method at ng/ml concentrations is known in the art and are found in the following papers which are an experimental indications that the SAW sensor specifically employed by this application, teaches that the LOD and SNR of the combined sensor and its reader cannot resolve the problem of the limitation of detector sensitivity: Bisoffi, Marco, et al. "Rapid detection of human immunodeficiency virus types 1 and 2 by use of an improved piezoelectric biosensor." Journal of clinical microbiology 51.6 (2013): 1685-1691; Bisoffi, M., et al. "Detection of viral bioagents using a shear horizontal surface acoustic wave biosensor." Biosensors and Bioelectronics 23.9 (2008): 1397-1403; Branch, Darren W. Love Wave Acoustic Array Biosensor Platform. No. SAND2011-0188C. Sandia National Lab. (SNL-NM), Albuquerque, N. Mex. (United States), 2011; Branch, Darren W., and Susan M. Brozik. "Low-level detection of a *Bacillus anthracis* simulant using Love-wave biosensors on 36 YX LiTaO3." Biosensors and Bioelectronics 19.8 (2004): 849-859; and Baca, Justin, et al. "Rapid detection of Ebola virus with a reagent-free, point-of-care biosensor." Sensors 15.4 (2015): 8605-8614.

What is needed is a method whereby an SH SAW detector in a microfluidic device may be employed to be able to claim FDA-compliant sensitivities of 2 pg/ml or lower.

BRIEF SUMMARY

The illustrated embodiments of the invention include a method of assaying an analyte in a sample in a portable, handheld microfluidic reader. The method includes the steps of: inserting the sample in the reader; capturing the analyte with a first antibody having a DNA tag attached thereto and with a second antibody attached to a magnetic nanoparticle or to a compatible surface; where a immuno-sandwich including the magnetic nanoparticle, first and second antibodies, the analyte, and the DNA tag is formed; replicating the DNA tag using isothermal amplification to a predetermined amount of DNA tags detectable by a detector; separating the amplified DNA tags from the rest of the sandwich; and measuring the amount of replicated DNA tags using the detector.

In the embodiment where the sample is a blood sample, the step of inserting the sample in the reader includes inserting the sample into a sample inlet on a microfluidic rotatable disc, and the method further includes the step of moving the blood sample into a blood plasma separation chamber in the microfluidic rotatable disc, and separating the blood into a plasma component including the analyte and a cellular or extracellular components.

The step of capturing the analyte in the sample with the first antibody having a DNA tag attached thereto comprises moving the plasma component including the analyte into a mixing chamber on the rotatable disc, mixing the analyte with the first antibody, and binding the analyte to the first antibody. Both a DNA covalently coupled antibody or a DNA linked antibody is contemplated as within the scope of the invention.

The method further includes the step of preloading the mixing chamber with the first antibody having the DNA tag attached thereto prior to moving the plasma component including the analyte into the mixing chamber on the rotatable disc.

The step of capturing the analyte in the sample with the second antibody includes the step of moving the plasma component including the analyte into the mixing chamber or an amplification chamber on the rotatable disc, mixing the analyte with the second antibody, and binding the analyte to the second antibody.

The method further includes the step of preloading the mixing chamber with the second antibody attached to either a surface or a magnetic nanoparticle prior to moving the plasma component including the analyte into the amplification chamber on the rotatable disc.

The step of capturing the analyte with the first antibody having a DNA tag attached thereto is performed before capturing the analyte in the sample with a second antibody attached to a surface or magnetic nanoparticle (MNP). or the step of capturing the analyte with the second antibody attached to a surface or MNP is performed before capturing the analyte in the sample with a first antibody having a DNA tag attached thereto, or the steps of capturing the analyte with the first antibody having a DNA tag attached and capturing the analyte in the sample with a second antibody attached to a surface or MNP are performed concurrently with each other.

If the second antibody is attached to a magnetic nanoparticle (MNP), the method further includes the steps of fixing the sandwich of the magnetic nanoparticle, first and second antibodies, the analyte and the DNA tag in the amplification chamber by activating a magnetic field extending to the amplification chamber, and removing unbound elements or contaminants from the amplification chamber while leaving the fixed immunoassay sandwich in the amplification chamber;

The method further includes washing the fixed immunoassay sandwich in the amplification chamber to flush the amplification chamber and to ensure only captured analyte is retained within the amplification chamber.

The step of replicating the DNA tag using isothermal amplification to a predetermined amount detectable by a detector includes the step of resuspending the sandwich in an amplification chamber in the rotatable disc in a buffer at a constant temperature including primers, base pairs and polymerase for a predetermined time to replicate the DNA tag.

The method further includes the step of maintaining the constant temperature in both the amplification chamber of the CD microfluidic disc with the resuspended immunoassay sandwich therein and the SH SAW sensor chamber of the disc with the DNA attached therein using an apparatus, such as a Peltier heater/cooler.

In the case where the detector is a surface acoustic wave (SAW) detector in the CD microfluidic disc, the method further includes the steps of moving the replicated DNA tags from the amplification chamber into the SAW detector and fixing the replicated DNA tags to a sensor surface of the SAW detector.

The method further includes the steps of removing unbound elements or contaminants from the sensor surface of the detector and spin drying the sensor surface of the detector by rotating the disc.

The step of replicating the DNA tag using isothermal amplification to a predetermined amount of DNA tags detectable by a detector includes the steps of controlling the time during which replication of the DNA tag is allowed, moving the replicated DNA tags from the amplification chamber into the detector and fixing the replicated DNA tags within the detector.

The method further includes the step of determining the amount of analyte in the sample from the amount of time allowed for replication and the measured amount of replicated DNA tags.

The illustrated embodiments of the invention also include an apparatus for assaying an analyte in a sample. The apparatus includes a portable, handheld microfluidic reader. The reader has a rotatable microfluidic disc. The disc includes: a sample inlet defined in the disc into which the sample is inserted; a mixing chamber defined in the disc and selectively communicated to the sample inlet and provided with a first antibody for capturing the analyte having a DNA tag attached thereto; and amplification chamber defined in the disc and selectively communicated to the mixing chamber and provided with a second antibody for capturing the analyte and either attached to the surface of the chamber or having a magnetic nanoparticle (MNP) attached thereto, where a sandwich including the surface or MNP first and second antibodies, the analyte and the DNA tag is formed; the amplification chamber is also used for replicating the DNA tag using isothermal amplification to produce a predetermined amount of DNA tags; a detector selectively communicated to the amplification chamber and provided in the disc for measuring the amount of replicated DNA tags; and several washing chambers communicated to the amplification and detector chambers containing washing buffer to flush the respective chambers.

In the illustrated embodiment the detector is a surface wave acoustic (SAW) detector, but optical and electrochemical detectors of various designs could be substituted.

Where the sample is a blood sample, the apparatus further includes a plasma-blood separating chamber having an inlet communicated to the sample inlet and an outlet for communicating plasma including the analyte to the mixing chamber.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 1 is a diagrammatic depiction of the steps wherein a bioanalyte is captured, sandwiched in an antigen pair having a magnetic nanoparticle and DNA tag which DNA tag is then amplified, the amplified mass of DNA transported to and attached to a SAW sensing chamber, and measured.

FIG. 5 is a top view diagram of a fourth step in the method of the illustrated embodiment, namely mixing of the analyte with the antibody-MNP complex.

FIG. 8 is a top view diagram of a seventh step in the method of the illustrated embodiment, namely resuspension of the complexes in an amplification buffer.

Figure 2:
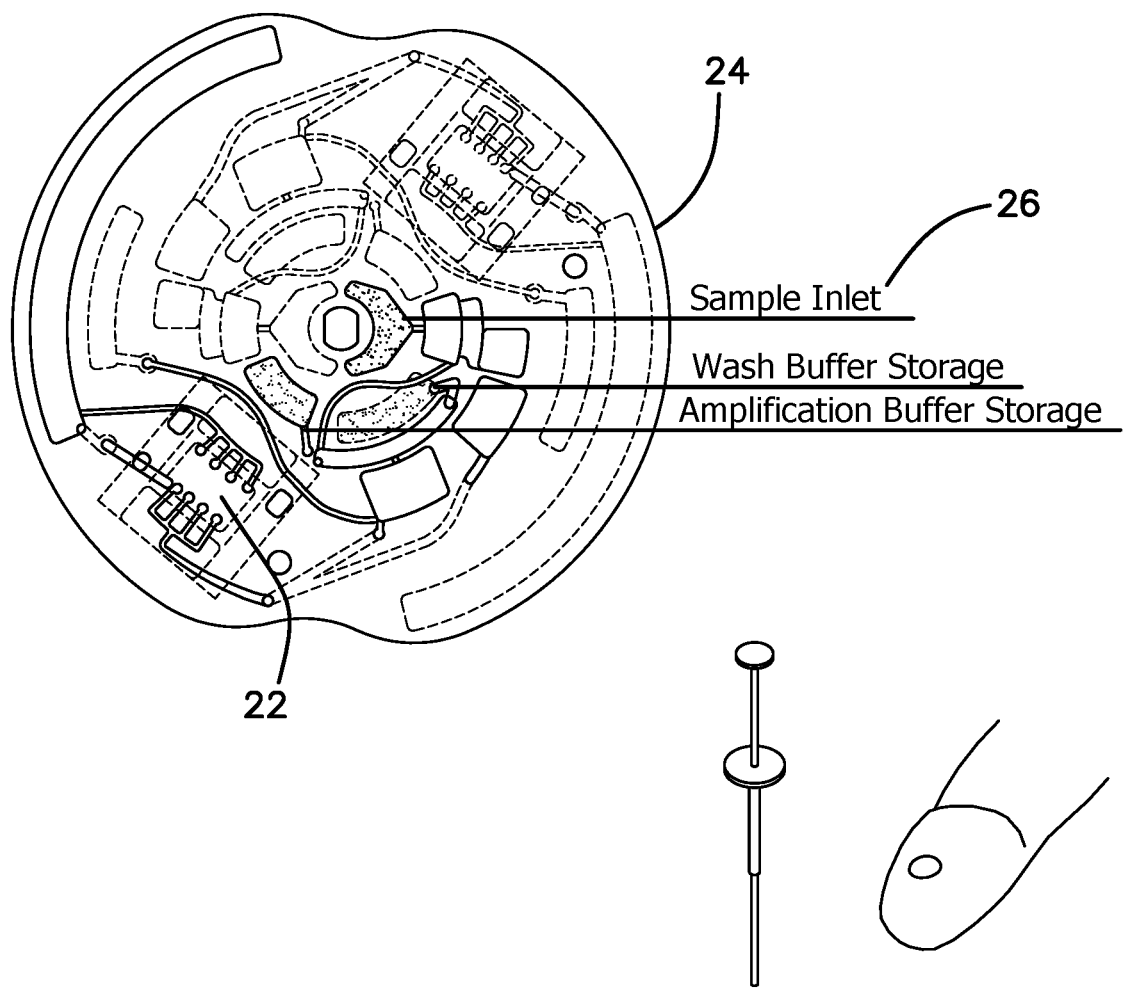
FIG. 2 is a top view diagram of a first step in the method of the illustrated embodiment, namely a sample insertion.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

In order to understand the inherent limitations on sensitivity for a SAW sensor for low volume or femtomolar samples, it is necessary first to review some basic definitions and conceptions relating to detector sensitivity and how FDA standards relate to them.

Theory and Operation, Limit of Detection & Sensitivity Analysis

The rapid autonomous detection of pathogenic microorganisms and bioagents by field deployable platforms is a significant benefit to human health and safety. To achieve a high level of sensitivity for fluidic detection applications, we have developed a 330 MHz Love wave acoustic biosensor on 36° YX Lithium Tantalate (LTO).

Detection is achieved by comparing the reference phase of an input signal to the phase shift from the biosensor using an integrated electronic multi-readout system such as noted by the Optiku™ platform defined further by U.S. Pat. No. 8,436,509, incorporated by reference in its entirety.

Limit of Detection, Sensitivity Limits, $S_m^\varphi$ Parameter

In describing the underlying principles of the SH SAW biosensing apparatus, we briefly outline the notion of limit of detection associated with the formation of the sensor, (a 330 MHz Love wave acoustic biosensor on 36° YX lithium tantalate (LTO)) and the problem presented by its inherent sensitivity, while providing a method and exemplary apparatus that resolve the problem of the lower limits of sensitivity, defined herein as the $S_m^\varphi$ parameter.

The $S_m^\varphi$ parameter is defined as the lowest sensitivity of the SH SAW 330 MHz device, where a floor signal-to-noise ratio (SNR) is obtained and where S is the sensitivity of the biosensing platform at its minimum detectable mass, m, relative to the detectible signal in percent of phase shift ($\phi$). When the output value of the device (($\phi$) is at least three standard deviations ($3\sigma$) above the output signal at the floor signal-to-noise ratio (SNR), such a signal is then considered as statistically representative of the detected mass. In this application where we employ an SH SAW, the corresponding output electrical signal is defined by the phase shift from a reference zero defined by a "Reference Lane" and the output is a differential result(s) of the consecutive time domain dependent arithmetical subtraction and curve fitting algorithm, which normalizes the discrete data points along the measurement(s).

FDA Guidelines for LOD, LOQ and MDL

The FDA "Guidelines for the Validation of Chemical Methods for the FDA FVM Program, 3rd Ed., 2019" identifies and mandates that the limit of detection (LOD) "is the minimum amount or concentration of analyte that can be reliably distinguished from zero." The term is usually restricted to the response of the detection system and is often referred to as the "detection limit". This definition is followed by the cross parameter defined as "limit of quantification" (LOQ): namely "the minimum amount or concentration of analyte in the test sample that can be quantified with acceptable precision", and is followed by a definition which applies to the measuring apparatus and its detector, where "method detection limit" (MDL) is the minimum amount or concentration of analyte in the test sample that can be reliably distinguished from zero by the instrument. MDL is dependent on sensitivity, instrumental noise, blank variability, sample matrix variability, and dilution factor. The $S_m^\varphi$ is a synthetic parameter comprising the ability of the detection instrument's limits to acquire a reliable signal (above the SNR floor) from the bioprobe on the surface of the sensor with the lowest concentration of an analyte.

This application teaches and demonstrates a method which enables one to overcome the detector's sensitivity parameter $S_m^\varphi$ by the integration of a DNA amplification technique coupled with the use of SH SAW biosensing apparatus that extends the platform sensitivity limits and provides for a reliable, FDA mandated LOD for the detection of early disease models where biomarkers such as troponin complex cTn, HIV1 and its signaling protein p24, p36 or HIV2 with its signaling protein p41, are secreted in bodily fluids, and where such indicators' concentrations of such biological species are manifested in values ranging from femtomolars to nanomolars of a analyte.

For a measurement to be deemed statistically significant by the National Institute of Standards and Technology (NIST), a signal value must be three times larger than its SNR. The LOD therefore that arises from this relationship as set forth by NIST, with the use of the operational frequency (325 MHz) with an apparatus output measured in phase ($\phi$) of the frequency is given by:

$$LOD = \frac{3 \times N_f}{S_{cr}^\phi \times \phi_0} \Delta\sigma_r.$$

where $S^\Phi_m$ is the sensitivity of the detector with reference to phase and standard deviation $\sigma_r$, $N_f$ is the operational frequency, $\phi_0$ is the unmodulated phase (reference) and $\phi$ is the phase measurement obtained from the surface acoustic wave sensor.

SH SAW Principle of Operation

The system's general specification, as we have discovered, shows that the Love wave acoustic array operates with a centered frequency at 330 MHz, and shifts to 325-328 MHz after application of silicon dioxide waveguides. The insertion loss is measured as −6 dB with an out-of-band rejection of 35 dB. The amplitude and phase ripple were measured as 2.5 dB peak-to-peak and 2-3° peak-to-peak, respectively. Time-domain gating confirmed propagation of the SH mode while showing suppression of a triple transit. Antigen capture and mass detection experiments demonstrate a sensitivity of 7.19±0.74° mm$^2$/ng with a detection limit of 6.7±0.40 pg/mm$^2$ for each channel with an SH-type wave propagating on 36° Y-cut lithium tantalate (LTO) along the x-axis which exhibits strong coupling ($K^2$=6.6%). The strong coupling on LTO provides advantages over substrates such as ST-Quartz where exquisite care in the fluidic packaging is required to prevent excessive wave damping and hence high insertion losses. This disclosure focusses on the use of such a SH SAW device, the testing of which indicates that our findings, observations and the obtained results, define an optimized platform. Each and every parameter associated with the physical and chemical aspects of the sensor and its electronic reader provide a basis and reason for the steps disclosed here as being necessary to achieve a universal analytical and portable laboratory for the detection of biological species in a field setting.

Sensor Detection Resolution do not Solve the Problem of a Limited $S_m^\varphi$ Sensitivity Parameter.

A description of the sensor electrical attributes is necessary in order to avoid an erroneous conclusion, with respect to the class of mass measuring devices such as Love wave biosensors, that if the sensor insertion losses could be reduced, that the SNR of reader electronics might be improved, or its analog-to-digital apparatus be augmented from 64 bit machine to a 128 bit processing time and its electronic clock provided by an attosecond metonym, the sensitivity problem might be addressed by such hardware fixes.

The solution proposed by the use of the DNA tag replication as disclosed below is a departure from the existing art and that with the use of theoretical as well as experimental data collected by our laboratory, we further provide evidence that improvements of the sensor characteristics as well as the reader electronics coupled with improved biochemical probes will not be a substitute for the disclosed solution.

The SH SAW in this disclosure, is based on the leaky SH-type wave propagating on 36° Y-cut lithium tantalate (LTO) along the x-axis which exhibits strong coupling ($K^2$=6.6%) and where the waveguide performance is defined experimentally through measuring the slope of degree change verses energy density in terms of frequency (°/MHz). The sensor's performance is verified by increasing the waveguide thickness of the waveguide until the slope is maximized relative to the lowest insertion losses measured in dB, thereby demonstrating the optimal waveguide performance. A comprehensive analytical treatment of the piezoelectric properties of a LTO biosensor is provided in A. Malavé, U. "Lithium tantalate surface acoustic wave sensors for bio-analytical applications," IEEE Sensors, pp. 604-607, 2006.

The optimization of the sensor performance demonstrates that once a limit of detection is defined by a method of diluting the analyte, which is a well defined process, where a series of known concentrations of analyte by volume are applied with consecutive dilutions of e.g. 240 ng/ml×10, 100, 1000, etc. and while such dilution is applied, the phase shift is measured relative to the signal-to-noise ratio by observing the error bar as a corresponding limit of dilution, until the output signal is observed and its corresponding error bar is equal to the signal magnitude. Thereafter, the lowest detectable concentration relative to the lowest SNR is identified and thus the lowest LOD is determined. This calibration method establishes the $S_m^\varphi$ parameter.

The bioengineering steps described below demonstrate the usefulness of creating an immunoassay with unique properties, namely the combination of two orthogonal antibodies for a specific analyte (e.g. troponin cTn I or T), where the first antibody is fitted with a magnetic nanoparticle bead and the complimentary orthogonal second antibody is fitted with a DNA tag (e.g. 215 base pairs). The immunoassay complex comprises a unique sequenced base pair and a primer.

DNA Tag with Unique Base Sequence and its Primer Specificity.

During our experimental phase of the a 36° YX lithium tantalate sensor a lab protocol was established that comprises the following variables:

a) Surface modification/salinization chemistry for immobilization of the various antibodies employed, full antibody and fragmented antibody (scFv), gold nanoparticles (GNP) of different sizes 10 nm, 30 nm, 100 nm etc.

b) The linker chemistry with different groups: thiolated, hydroxylated, carbonylated.

c) Additional techniques, such as the use of IgG1 antibody sites for conjugation (thiol, amine and carbohydrate), were further employed in generating the antibody-biotin conjugates, including chemical scaffolding with varying length of linker types were also used in conjugating biotin to the antibody (N-hydroxysuccinimide with different spacer arms including maleimide or biotin.)

During the trial period all these variables are analytically separated and tested for their relative contribution to the outcome, i.e. measuring the output phase shift relative to concentration, followed by successive dilutions (×10, ×100, ×1000 etc.). We observed that the total output while employing the iterative combinations above and came to a clear and terminal conclusion: The resolution of the combined biochemical probe with the biosensor under multiple scenarios of different waveguides thicknesses and different compactions over the sensing layers including different pH conditions, resulted in LODs:

$4\times(10^{-9})$ nanogram per milliliter under a wet-wet chemistry condition, or $12\text{-}24\times(10^{-12})$ picogram per milliliter under wet-dry chemistry conditions.

The results of our experimental data were clear, no optimization on the chemical probe or its artificial amplifier such as gold nano particles (GNP) or magnetic nano beads (MNP) with the combinatorial chemistry noted above was able to improve the resolution of the system beyond its SNR limits.

The conclusion above closely resembled the theoretical limits set by the predictive algorithm detailed by Darren et al (Sandia National 2008-6128 DOE) section 1.4.1 "Generalized Green's function for 36° YX LTO" where the authors conclude that under their study they " . . . developed a suite of modeling codes to simulate and optimize SAW devices. These include Green's function analysis, effective permittivity analysis, 2D and 3D FEM, multilayer isotropic dispersion models, and exact mass sensitivity models. These analytical parameters lead to the development of an IDT design for high frequency (>300 MHz) Love wave sensors on 36° YX LTO. The IDT design minimized bulk wave interferences, achieved a highly linear phase response (2.8° P-P), and eliminated the need for impedance matching. The design was used to create a four channel Love wave array biosensor on a single die." The study concludes by stating that the theoretical sensitivity analysis demonstrated that isotropic models are insufficient to predict sensitivity for 36° YX LTO. Mass sensitivity results demonstrate the ability to detect at the pg/mm² level depending on the noise and resolution of the phase measurement hardware.

This conclusion and our experimental work which include a consecutive-iterative steps of optimization on the 36° YX LTO, on its waveguide thickness, the bioprobe combinatorial structure, (full antibody, scFv, antibody-compaction, antibody-directionality, affinity and avidity of critical domain) were all explored in an efforts to increase resolution and alter the inherent limitation of the sensitivity measure $S_m^\varphi$.

As is made clear the fields of biology and specifically the discipline of diagnostic biochemistry, it is demonstrable that the proposed technique of DNA tag replication incorporated into the CD microfluidic and its reader platform, Optikus™, provide an effective procedure for the detection, capture and reporting of an analyte concentration without any limitation of a starting concentration. For example, assuming a circulating DNA, RNA VIRUS, or small protein are present with mass value of a femtogram ($10^{-15}$), the disclosed method allows reliable detection, where the theoretical limit of the system is $S_m^\varphi \geq$ sensitivity of 7.19±0.74° mm²/ng with a detection limit of 6.7±0.40 pg/mm².

Sensor Boundary Conditions Minimal Mass Loading $S_m^\varphi$

Figure 15:
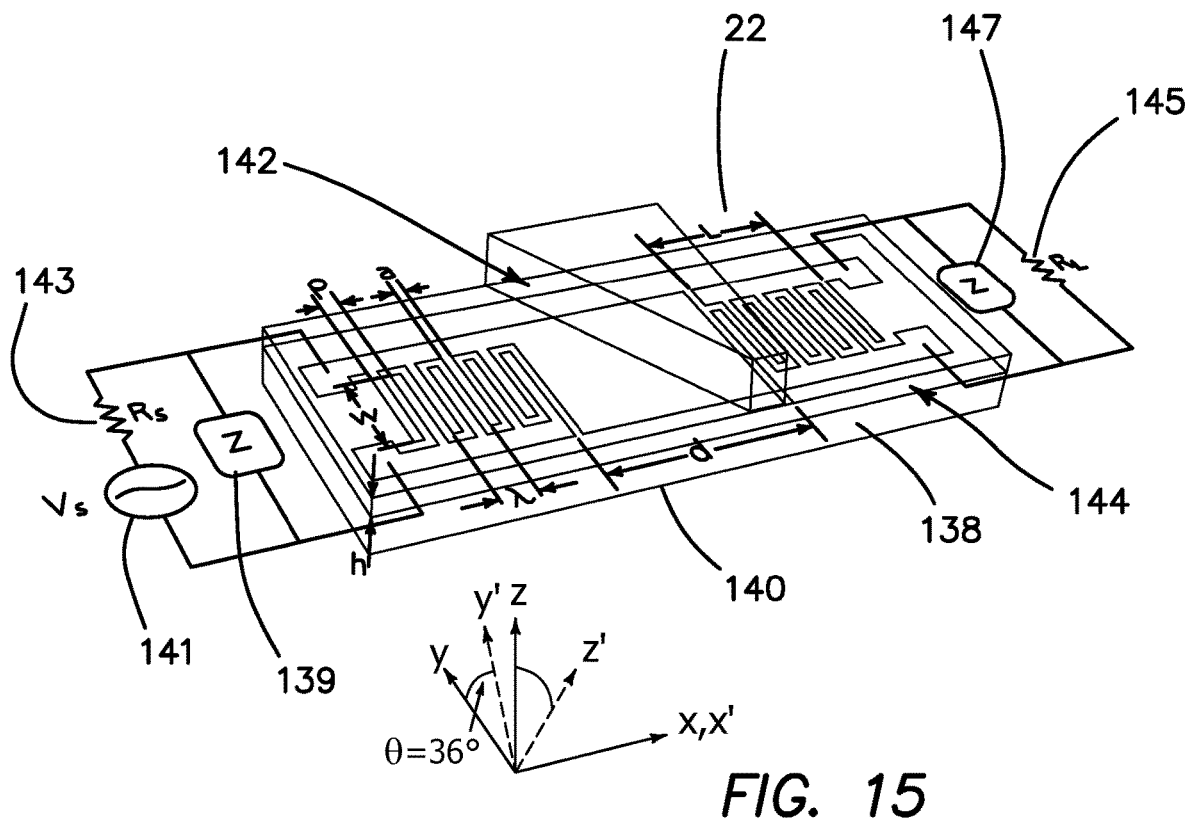
FIG. 15 is a perspective view of a 36° YX lithium tantalate device with the geometry and wave propagation coordinates of the shear horizontal surface acoustic wave sensor as employed in the illustrated embodiments.

A Love wave biosensor on 36° YX lithium tantalate is shown in FIG. 15, with a simple interdigital transducer (IDT) geometry having a uniform strip or finger width a, periodicity p and a metallization ratio of 0.5 (η=a/p). In practice, the IDTs often have a far more complex geometry to reduce coupling between the surface skimming bulk waves (SSBW) and excitation of the longitudinal mode. The center frequency is computed from the strip width and acoustic velocity for the crystal type and orientation. The IDT design of the sensor and its properties are illustrated schematically for the purpose of illustrating that the limitation of the sensor sensitivity measure is bound by the frequency domain, insertion loses, geometry, number and length of the sensing lanes, the waveguide material and geometry, the fabrication technique and the environmentally induced effects of temperature and other pertinent parameters, which are well identified by the study conducted by Sandia National Laboratories, Darren W. Branch et al. Shear Horizontal Surface Acoustic Wave Microsensor for Class A Viral and Bacterial Detection".

The description of the SH SAW with its 36° YX lithium tantalate is shown for illustration in this disclosure for the purpose of demonstrating that continuous improvement of the sensor substrate, its frequency domain, its reduced insertion losses and the use of an improved detector electronics (the use of an Analog to digital converter with 64 bit machine vs. a A/D with 24 bit resolution) cannot provide a solution to the inherent physical problem of limited sensitivity measure $S_m^\varphi$. The limitation of the sensitivity measure $S_m^\varphi$, can be overcome by the disclosed method of this application, where this application teaches a method by which we can "dial back" the machine resolution by the introduction of DNA tag replication, such is commonly known as polymerase chain reaction (PCR) or the alternate method such as Loop-mediated isothermal amplification (LAMP), to create a mass equivalent unit proportional to the concentration of the analyte in question.

The only parameter that limits the biosensor and its resolution is the minimum mass and its density per unit of sensor surface area as indicated above. The antigen capture and mass detection experiments demonstrate a sensitivity of the SH SAW with 36° Y cut and X propagation employing a lithium tantalate piezoelectric substrate with resolution 7.19±0.74° mm²/ng and with a detection limit of 6.7±0.40 pg/mm² for each channel. This sensitivity level of 6.7 pg/mm² is inherently part of the physical limits of the sensor and it is driven by the mass density layered over the sensing lane. Our discussion of such limit of minimum mass is than solved by the DNA tag replication methodology disclosed here.

Acoustic waves must satisfy both Newton's and Maxwell's equations. In the absence of external forces, the equations are expressed as:

$$\rho \frac{\partial^2}{\partial t^2} = \nabla \cdot T, S = \nabla_S u, \nabla \cdot D = \rho_f$$

where ρ is the mass density, u is the particle displacement, and T and S are the surface stress and strain components, respectively. D and pf are the electric displacement and free charge density, respectively. The free charge density ρf is zero everywhere except at the surface of the substrate. Coupling the fact that the mass density ρ is the dominant factor in setting up the sensitivity measure $S_m^\varphi$ we than proceed to the solution proposed by the application where a DNA tag replication enable the creation of an equivalent mass proportional to the concentration of the analyte in question.

Mass Sensitivity Analysis

The solution shown in the illustrated embodiments of the invention is made clear by considering the limitations imposed by a SH SAW biosensor in detecting a picogram of analyte in a milliliter of liquid, in which a biological specie is not detectable when the limit of detection of the electronic apparatus and its SNR floor have an equal or larger error bar then the registered value obtained. Hence, the statistical significance of the measurement is thus rendered as unreliable, non-reproducible and therefore fails to meet the scientific guidelines defined by the FDA for LOD, LOQ and MDL.

The reliability of the measurement is thus ultimately considered outside the accepted threshold defined by the FDA. In the discussion that follows, we explain the physical limitations of currently available SH SAW sensor class with their inherent limitation as defined in this application as $S_m^\varphi$ and where we address the steps that lead to overcoming such electrical, biological and detection limitations. The disclosed method increases the sensitivity of the SH SAW platform by reliably dialing back the necessary value of the threshold value to overcome the minimum ρ in pg/mm² to render the existing class of mass measurement biosensors of chemical scales using surface acoustic devices SH SAW (as described above) into an instrument class that has an output and sensitivity which is not the dependent on the inherent limitation of its sensitivity i.e. the minimum mass loading (on the mass layer) to reliably generate a phase change as a measure of the concentration of analyte and with a dynamic range as low as femtomolar to nanomolar concentration levels in milliliter.

Mass Sensitivity

Figure 15A:
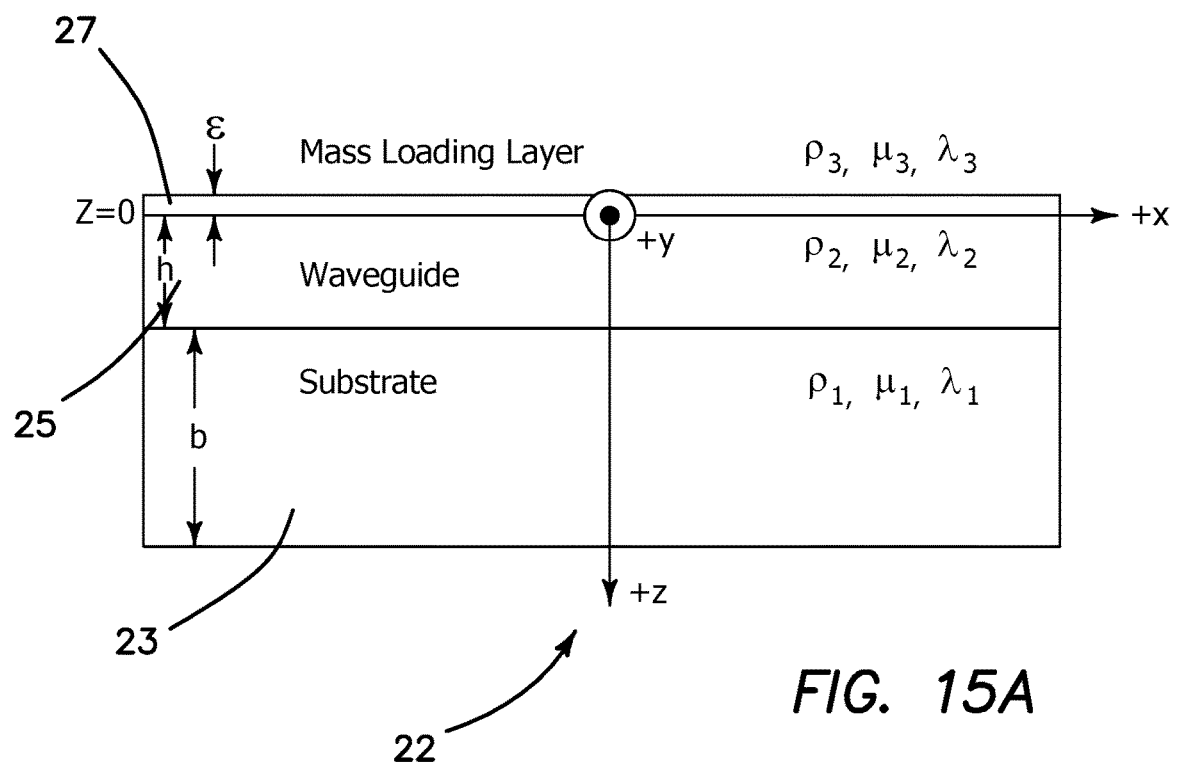
FIG. 15A is schematic representation of the SAW sensor, whereby the composite structure is shown with a finite substrate, which resembles physical devices and also extends the analysis to include perturbations at both faces of the composite structure.
Figure 16:
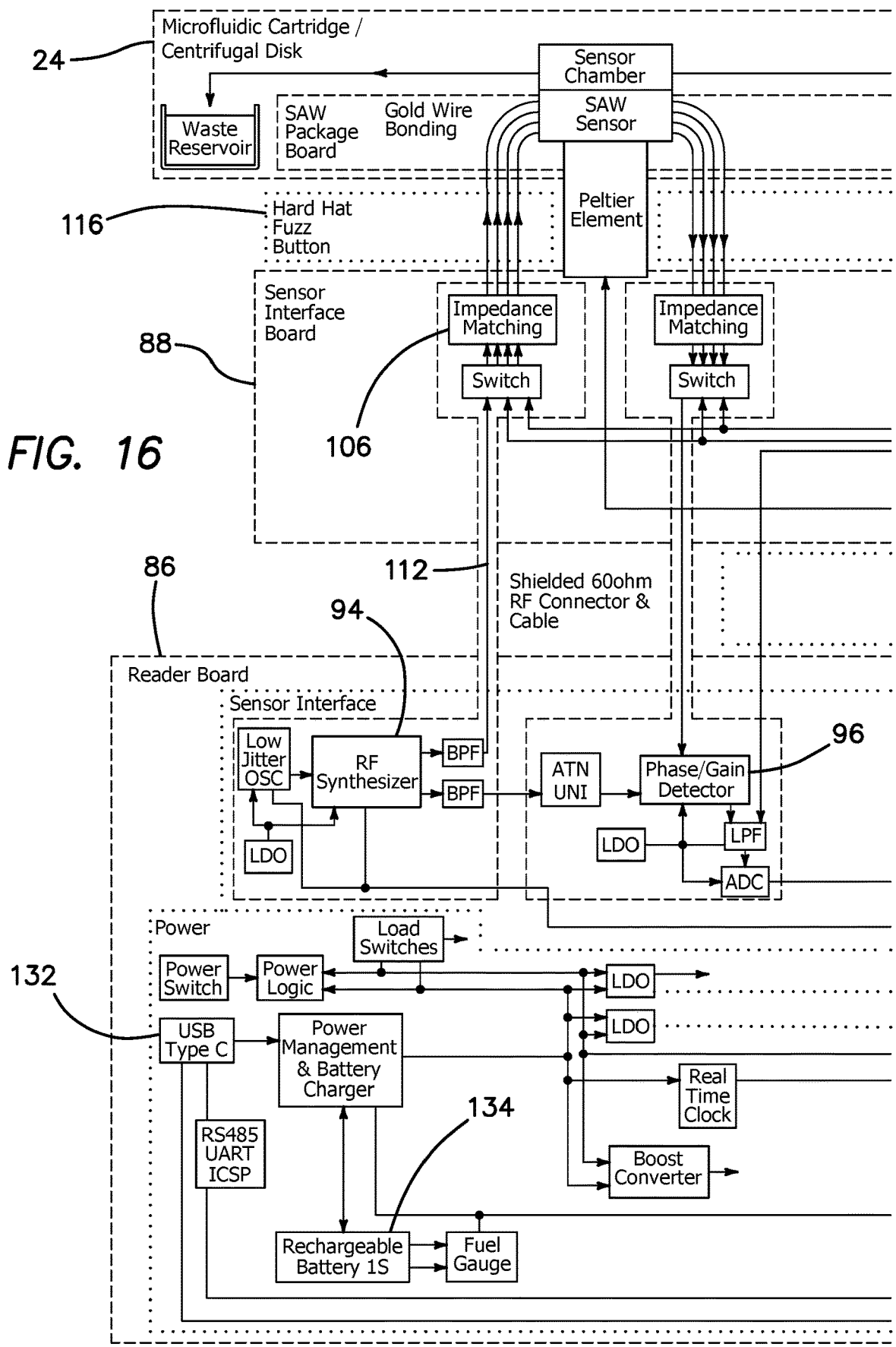
FIG. 16 is a schematic diagram of the Optiku™ platform where the block diagram describes the functional relationships in circuits used to perform the amplification method that enables the increased sensitivity measure $S_m^\varphi$.
Figure 16:
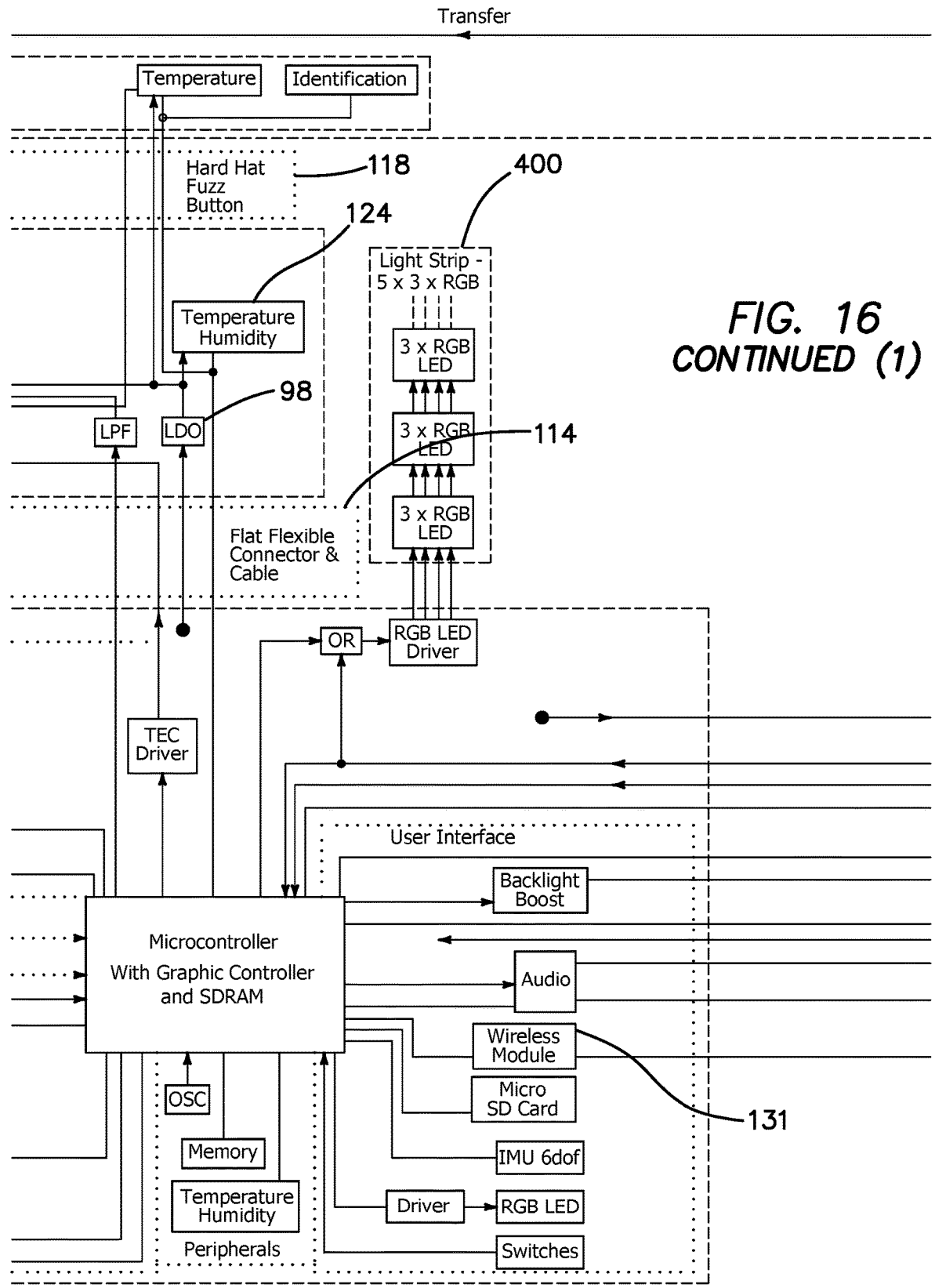

Gravimetric sensors are usually configured in two types of instrumentation: namely 1) oscillation frequency measurements and 2) phase velocity measurements. For SAW delay lines the sensitivity is defined as a measure of the intrinsic properties of the device as shown by S. W. Wenzel et al. "Analytic comparison of the sensitivities of bulk-wave, surface-wave, and flexural plate-wave ultrasonic gravimetric sensors," Appl. Phys. Lett., vol. 54, pp. 1976-1978)

$$S_m = \frac{1}{V_0} \lim_{\Delta m \to 0} \frac{\Delta V}{\Delta m}$$

where $V_0$ and $V$ are the unperturbed and perturbed phase velocities on the SAW device with $\Delta V = V - V_0$. The perturbation is an infinitesimal thin mass layer $\Delta m = \rho_x \varepsilon$, where $\rho_x$ is the density and s is the thickness of the mass loading layer as shown in FIG. 15A.

From this perturbation the mass sensitivity for the SH mode can be derived. Substituting the $S_m^\varphi$ phase with the attenuating energy $S_m^V$, the acoustic velocity in the bound mass layer is then given in terms of the mass sensitivity and is also dependent on the acoustic properties of the bound mass layer.

A mass sensitivity was determined for the Love wave sensors using calibrated fluids with known density and viscosity (a detail description of the relation between a SAW sensor design and its sensitivity and resolution is detailed in A. Malavé, et al "Lithium tantalate surface acoustic wave sensors for bio-analytical applications," IEEE Sensors, pp. 604-607, 2006. Four fluid samples were prepared with known amounts of glycerin and applied to the sensors. Subsequently, the phase shift was measured after each injection and repeated four times. The resulting slope $$\frac{\Delta \varphi}{\sqrt{\rho \eta}}$$

was determined by a linear fit procedure and used to calculate mass sensitivity and the detection limit for a given noise level and phase resolution.

In order to detect a virus reliably at concentration of 1,000 particles instead of the 100,000 particles as detected by the sensor typical of the prior art some form of an amplification scheme is necessary according to the illustrated embodiments of the invention. As described in more detail in the method noted by FIG. 1, the replication of a DNA tag within 10 minutes or 30 cycles or more will allow for a sufficient mass to be detected by the SH SAW for early infections of Ebola Zaire virus. To comply with FDA standards regarding signal quality, significantly more replications occur to generate a surplus of detectable mass meeting the threshold of an acceptable output or measured signal of three times the standard deviation of the background noise.

FIG. 1 is a diagrammatic depiction of the steps undertaken in a microfluidic circuit, such as shown and described in the Incorporated Disclosure, the disc 24 of which is explicitly shown in FIGS. 2-11, wherein an analyte 10 is specifically captured by a first antigen 14, which is coupled in turn to the surface of the disc or a magnetic nanoparticle 12. The steps in FIG. 1 may be practiced manually on a lab bench, but the illustrated embodiment is defined as being performed in a programmable, field portable microfluidic reader 62, shown in the Incorporated Disclosure, which can be operated by an operator with no or little medical or laboratory trainer. The analyte 10 is then attached to a second antigen 16 so that analyte 10 is sandwiched in an antigen pair 14, 16. The second antigen 16 has a DNA tag 18 attached thereto. In the illustrated embodiment the DNA tag 18 is a synthetically fabricated DNA sequence of about 200 base pairs using a DNA sequence which never or at least rarely occurs in nature. In this manner, DNA tag 18 is virtually guaranteed not to interact with any other biomolecules, particularly with any component in human serum or blood, but which can be easily linked to second antigen 16 through cysteine or other chemistry. If a magnetic nanoparticle is used in the second antibody, a magnetic field interacting with magnetic nanoparticle 12 is used to fix in position all copies of sandwich 14, 16, to which analyte 10 has been captured. If the second antibody is bound the surface, no magnet needs to be used. Any excess antigen 16 carrying DNA tag 18 not sandwiching analyte 10 with first antigen 14 is removed or washed away. The DNA tag 18 is then amplified using an isothermal amplification process. The degree of amplification of DNA tag 18 can be variably controlled by controlling the time allowed for isothermal DNA replication. The amount of DNA tag 18 can thus be selectively amplified by many orders of magnitude compared to the amount of attached DNA tag 18 present initially. The amplified DNA tag 20 is free floating and not attached to second antigen 16. The amplified mass of free-floating DNA tag 20 is separated from the fixed sandwiches 14, 16, transported to and attached to a sensing chamber of SAW 22 where it is measured. From the amount of measured DNA tag 20 and the known controlled degree of amplification, the amount of attached DNA tag 18 can be precisely determined and correlated back to the amount of captured analyte 10. Thus, it can be readily appreciated that even if the concentration of analyte 10 is 2 pg/ml or less, the corresponding amount of attached DNA tag 18 can be nearly arbitrarily amplified or replicated to an amount which is reliably and readily measurable by the SAW sensor 22 in either a wet or a dry configuration.

Turn now and consider the electronic data and signal processing circuitry used in the field portable microfluidic system in which the illustrated embodiments are realized. As a brief and high-level summary of the associated electronics with the microfluidic cartridge, turn to FIG. 16 which is a functional block diagram of the Optikus device, which is more completely detailed and described in the Incorporated Disclosure, U.S. Pat. Pub. 2019/0201900. The system and microfluidic cartridge comprise the following subsystems. A subsystem including a microfluidic CD 24, containing the SAW 12, and associated electronic connections. A sensor interface board 88 which contains the electronic RF components such as switch and impedance matching circuit 106 and the Fuzz button 116 to make electrical contact with the microfluidic CD 24. The board 88 is located on the Z stage 126 of the device. A light strip board 400 contains the RGB LEDs to illuminate or operate on the microfluidic CD 24 synchronously with the rotation of the microfluidic CD 24. A microfluidic board 300 contains all the electronics to control the position and speed of three motors as follows: 1) all the electronics to control position and speed of the microfluidic CD 24 provided by the three motors, 2) for the Z stage and 3) for the linear actuator of the laser 130. The board 300 also includes a driver to control a Peltier element 100 for thermal regulation in DNA amplification. Board 300 includes an optical system 128 to measure biological fluid concentrations (such as plasma) for quality purposes. A sensor interface board 88 is connected reader board 86 via a shielded RF connector and flex cable 112. The reader board 86 contains all the necessary electronics such as the RF signal generator 94 and detector 96, power management from USB connector 132 and battery 134, user interface (display, touch screen, speaker, microphone) and Wi-Fi/BLE 136 communication module for connecting to the cloud 64.

In the illustrated embodiment, a conventional isothermal nucleic acid amplification technique (LAMP) is used. However, it is to be expressly understood that other isothermal amplification techniques or even PCR methods could be adapted to the illustrated embodiments. In contrast to the polymerase chain reaction (PCR) technology in which the reaction is carried out with a series of alternating temperature steps or cycles, isothermal amplification is carried out at a constant temperature, and does not require a thermal cycler. In LAMP, the target sequence is amplified at a constant temperature of 60-70° C. maintained in the illustrated embodiment using a Peltier element and using six sets of primers and a polymerase with high strand displacement activity in addition to a replication activity. Typically, 4 different primers are used to identify 6 distinct regions on the target gene, which adds highly to the specificity. An additional pair of "loop primers" is used to further accelerate the reaction. Due to the specific nature of the action of these primers, the amount of DNA produced in LAMP is considerably higher than PCR-based amplification.

For example, in the illustrated embodiment where analyte 10 is troponin, a marker for cardiac infarction, each capture troponin protein can be associated with a unique DNA tag 18, which can readily be amplified by a factor of $10^9$ resulting in an easily measurable corresponding amount of free DNA tag 20 from which the amount of captured troponin is accurately and precisely determined. For the following calculations, the assumptions in the table below are used:

| Assumption | Value |
| --- | --- |
| Minimum Troponin level detectable on SAW without mass enhancement | 45 µL of a 1 µM solution |
| Mass of Troponin subunit | ~25 kDa per troponin molecule |
| Mass of 215 bp DNA strand | ~150 kDa per DNA strand |
| Minimum clinically relevant Troponin concentration we need to detect | 45 µL of 1 fM solution |

A 45 µL sample of 1 µM solution of troponin contains about 1120 ng of troponin. If the unique DNA tag is 215 bp in length, replacing each troponin molecule with a DNA segment, results in $4.5 \times 10^{12}$ DNA segments or 1120 ng of DNA. This amplification factor will yield ~25 ng/mL of DNA on the sensor surface, well within the limit of detection of the SAW sensor. In another example, 1 µM of troponin is a mass known to be detectable on the currently available Optikus™ detector. About $10^{11}$ copies of 215 base-pair DNA tags has the same mass as 45 µL of 1 µM solution of troponin (known to be detectable by the SAW). If we start with an troponin sample and concentration of 1 µL of a 1 fM solution (a concentration corresponding to the lowest amount of troponin required to be detected by current commercial standards), this sample and concentration results in about 602 molecules of troponin. If we assume that the first antibody with attached DNA tag captures the troponin target in a 1:1 ratio, we will have 600 ($6 \times 10^2$) DNA tags/µl of liquid prior to amplification. To go from about $6 \times 10^2$ captured DNA tags 18 to $10^{11}$ DNA tags 20 on SAW 22 (an easily measurable mass) requires about 30 replication cycles of isothermal amplification (amplification by $10^9$), which takes about 10 minutes of time under the current LAMP assay. Isothermal amplification is a continuous process that does not have discrete cycles in the normal sense. These number are projected and are determined based on the specific primers, template and conditions used. Additionally, the estimate is Also it is highly likely that the capture will not be 100%. Thus, by employing the DNA amplification strategy, we can easily detect concentrations of Troponin down to the femtomolar range with the current capabilities of the SKC SAW device and the SKC Optiku™ platform.

Consider for the moment some aspects of the SAW device used in the illustrated embodiments. FIG. 15 is three-dimensional representation of a Love wave biosensor on 36° YX lithium tantalate with their Euler's rotation angels (0°, −54°, 0°). The shaded regions show a simple IDT geometry 138 having a uniform IDT strip width, a, and an IDT periodicity, p, and a metallization ratio of 0.5 (η=a/p). The piezoelectric substrate 140 has a polished upper surface on which two IDTs 138 are deposited using photolithographic methods. The left-hand input transducer as shown in FIG. 15 is connected, via fine bonded leads, to an electric source 141 (Vs) through an electrical matching network 139 and source resistance 143, (Rs). The righthand output transducer as shown in FIG. 15 drives the load 145 (RL), usually 50 ohms, through another electrical matching network 157 (Z). The center frequency (fc) is governed by the Rayleigh wave velocity (VR) on the piezoelectric substrate 140. For SAW devices, the velocity of wave depends on the properties of the piezoelectric crystal 140 and its crystallographic orientation.

In biosensor applications a flow cell is essential to confine the fluid and prevent electrical breakdown at the bonding pads. The fluid 142 is confined between the IDTs 138 by a specialized flow cell (not shown). In addition to the flow cell, a thin dielectric layer 144 is deposited on the piezoelectric substrate 140 to reduce changes in capacitance from the dielectric media. The application of the dielectric insulation layer 144 also serves as a guiding layer to enhance sensitivity, performance, and permit chemical attachment of recognition films for specific detection applications Acoustic waves must satisfy both Newton's and Maxwell's equations. In the absence of external forces, the equations described above and as are expressed as $$\rho \frac{\partial^2}{\partial t^2} = \nabla \cdot T, S = \nabla_S u, \nabla \cdot D = \rho_f$$

From this expression by the canonical representation of mass displacement, where we observe that the dominant element that drives the resulting value is the magnitude of the ρ (the mass density). The method by which we overcome the sensitivity measure arises from realizing that the sensitivity parameter of the entire system is defined by the ability of the SH SAW piezoelectric sensor 22 to overcome the limitations of minimum mass loading to affect the output electrical signal above SNR, such as the noise floor as measured by observing the lowest signal provided in a differential mode relative to a reference lane.

FIG. 15A is schematic representation of the SAW sensor 22, whereby the composite structure is shown with a finite substrate 23, which resembles physical devices and also extends the analysis to include perturbations at both faces of the composite structure. Using an analytic expression for the sensitivity can be calculated for the SH-SAW propagating modes by computing the shift in velocity ($\Delta V/V$) due to the addition of a thin mass loading layer 27, $\Delta m$, on the waveguide 25. In the substrate 23 and waveguide 25 the displacements are taken to be determined by the mass density $\rho$ while all characteristics of the LTO 36° YX, (0°,−54°,0°) which are the Euler angles, velocity of 4077 m/s and with $K^2(\%)$ set at 7(%) are all equal.

The conclusion associated with the theoretical predicted value and the resolution of the sensor resulting in 6.7±0.40 pg/mm$^2$, provides the reason why the method of the disclosure is a departure from the existing art. The fact that the method proposed of DNA tag amplification within the microfluidic CD is able to solve the minimum mass required to overcome the hardware and concentration dependent limitations set by the $S_m^\varphi$ parameter as described above.

FIG. 2 is a top view diagram of a first step in the method of the illustrated embodiment as carried out in a rotatable microfluidic disc 24 and reader 62 (symbolically depicted in FIG. 13), similar to that shown and described in the Incorporated Disclosure. FIGS. 2-11 shown an embodiment in which there are two microfluidic circuits fabricated into disc 24. The two microfluidic circuits may be identical or may be adapted to selectively assay different analytes 10 under program control. The first step is a sample insertion, such as a drop of blood from a finger prick, into sample inlet 26. In the microfluidic circuit, as shown in FIGS. 2-11, there are multiple chambers connected by a corresponding multiple number of conduits, channels or capillaries (hereinafter commonly referenced as "conduits".) Centrifugal force created by the rotation of disc 24 is used to transport the fluid through the conduits and chambers described below. In many cases, a conduit may be provided with one or more valves as needed to selectively control flow of fluid through the conduit, or in the case of a conduit which small enough to act as a capillary, the combination of capillary and centrifugal force is used to selectively flow a fluid through the capillary. In other instances, a black polymer film or adhesive plug may be disposed in the conduit. Disc 24 is rotated until the plug is positioned opposite a solid-state laser in the reader 62, which is selectively activated by software control to melt the plug away via laser ablation and thus selectively open the conduit. More detailed disclosure concerning these types of valves is discuss in the Incorporated Disclosure.

Figure 3A:
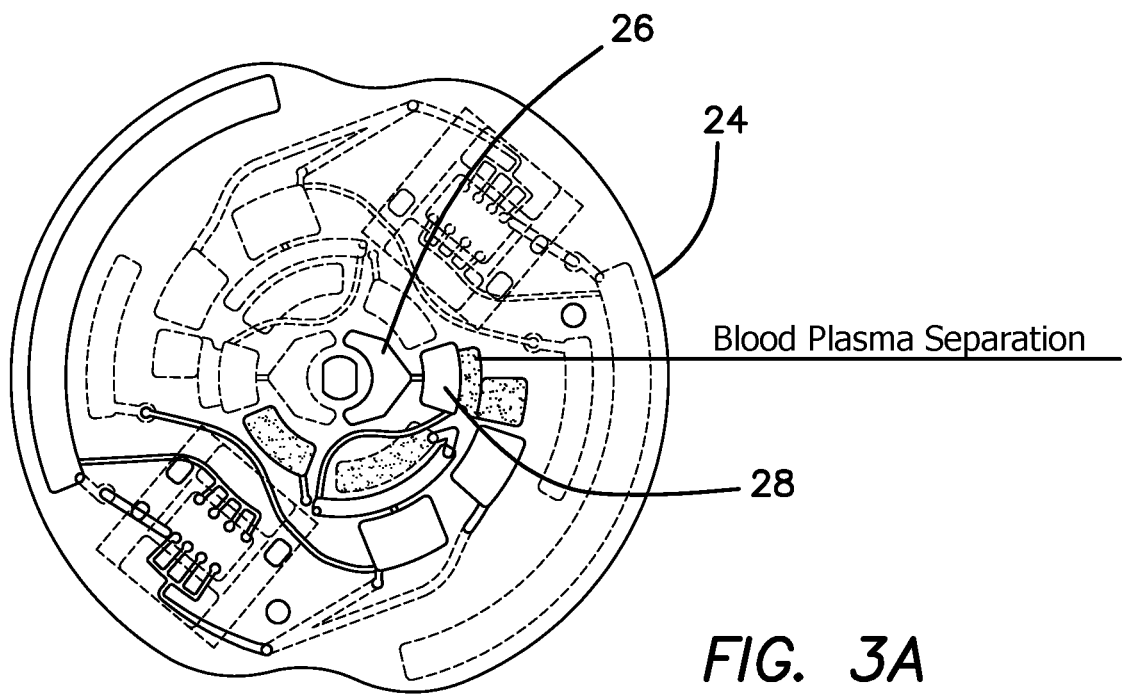
FIG. 3a is a top view diagram of a second step in the method of the illustrated embodiment, namely a blood-plasma separation.
Figure 3B:
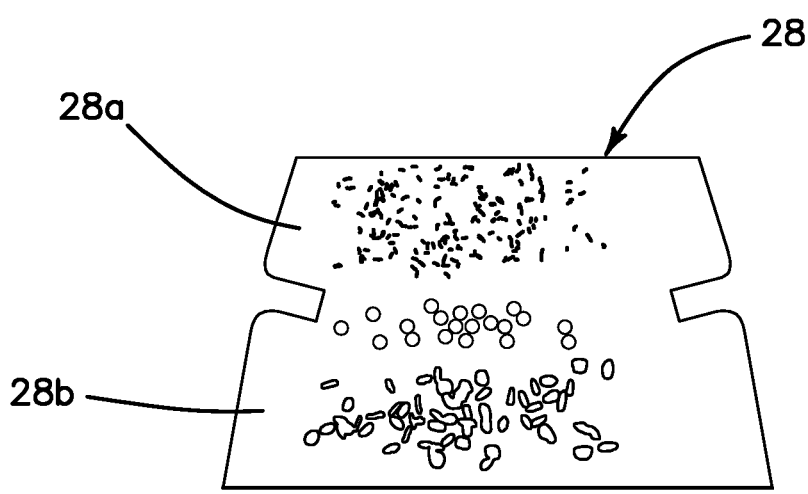
FIG. 3b is an enlarged top view of the blood-plasma separation chamber after the disc has been spun and the blood and plasma separated.

FIG. 3a is a top view diagram of a second step in the method of the illustrated embodiment, namely a blood-plasma separation. The steps of the disclosed method here and below are similar to those disclosed in the Incorporated Disclosure, which should be referenced for further detail when needed. Disc 24 is rotated at predetermined or pre-programmed rate above 3500 RPM (>500 g), and time, e.g. 60 s to 300 s, to transport the sample from sample inlet 26 into a two-part blood-plasma separation chamber 28. As shown in FIG. 3b the heavier components of the blood, the hemoglobin and platelets, move down to lower portion 28b of chamber 28, while the lighter components, the plasma or serum mixed with the biomarkers or analyte 10 or in the illustrated embodiment, troponin, remains in upper portion 28a.

Figure 4:
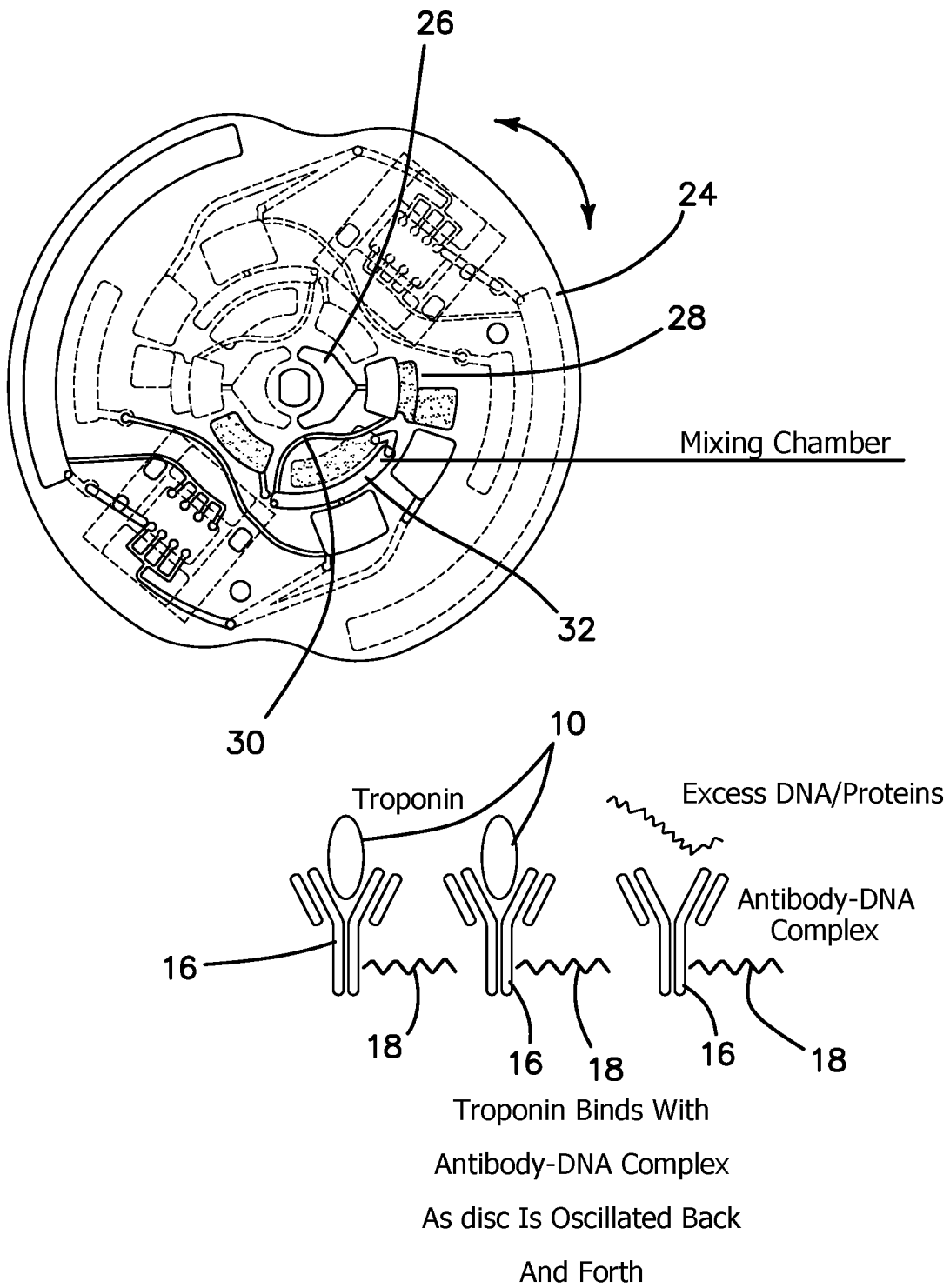
FIG. 4 is a top view diagram of a third step in the method of the illustrated embodiment, namely mixing of the analyte with the antibody-DNA complex.

FIG. 4 is a top view diagram of a third step in the method of the illustrated embodiment, namely mixing of the analyte 10 with the antibody-DNA complex 16, 18 in a mixing chamber 32. Programmed rotation of disc 24 for a predetermined time, e.g. 10 s to 90 s, and at a predetermined rate, e.g. 0 rpm to 500 rpm, transports the lighter components, including analyte 10, from chamber 28a through conduit 30 into chamber 32. Chamber 32 is provided or preloaded with the lighter antibody-DNA complex 16, 18. Analyte 10 binds with antigen 16 DNA tag 18 in mixing chamber 32 as disc 24 is oscillated at 0.5-2 Hz through a rotation angle of 30-360°, for a first predetermined time, e.g. 30 s to 180 s, arranged for the lighter antigen 14 and DNA tag 18.

FIG. 5 is a top view diagram of a fourth step in the method of the illustrated embodiment, namely mixing of the analyte 10 with the second antibody bound to either a surface or to an NP or MNP 12, 14. Chamber 40 is provided or preloaded with the second antibody complex 12, 14. Analyte 10 binds with antibody 14 potentially carrying an NP or MNP 12 in amplification chamber 40 as disc 24 is oscillated at a second predetermined rate, 0.5-2 Hz through a rotation angle of 30-360°, for a second predetermined time, e.g. 30 s to 180 s, to take account of the complex comprised of optional NP or MNP 12 and antigen 14. The end result is that a DNA tag 18, first antibody 16, analyte 10, second antibody 14 and either surface or magnetic nanoparticle (MNP) 12 are combined in a sandwich, which can be manipulated as a unit. There may be some overlap of the binding and mixing steps of antibody-DNA tag complex 10, 16, 18 and antibody-surface or MNP complex 12, 14 or the third and fourth steps may be performed in reverse order or combined into a single step.

Figure 6:
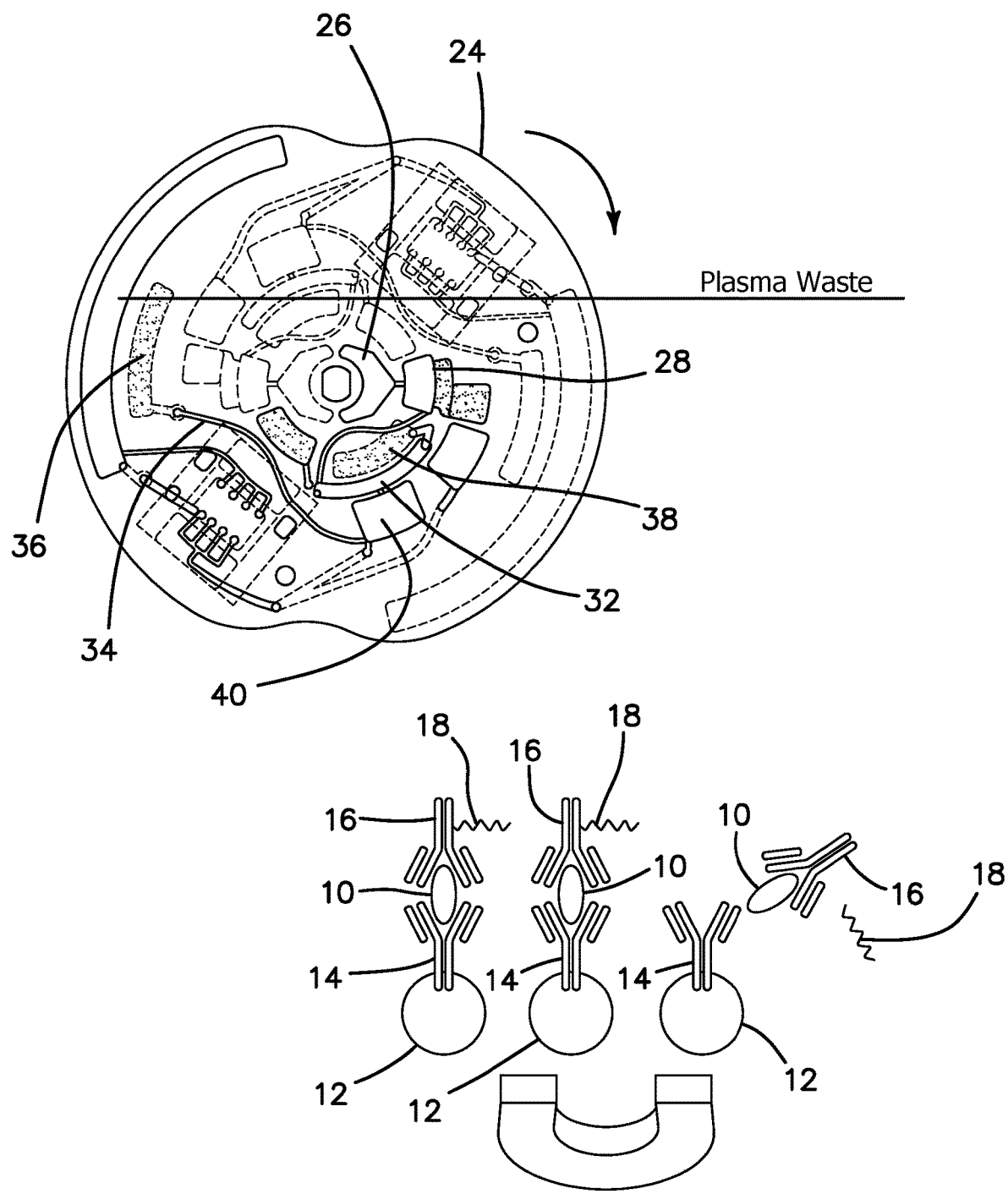
FIG. 6 is a top view diagram of a fifth step in the method of the illustrated embodiment, namely removal of the plasma and unbound contaminants.

FIG. 6 is a top view diagram of a fifth step in the method of the illustrated embodiment, namely removal of the plasma and unbound contaminants. If the complex uses an MNP bound to the second antibody, a magnet (not shown) underneath or near disc 24 is moved or energized to be magnetically operative in chamber 32, thereby drawing down or fixing antibody-MNP-analyte-antibody-DNA tag complexes 12, 14, 10, 16, 18 in chamber 40. If the complex is bound to the surface of 40, no additional components are needed. Disc 24 is then rotated to transport the plasma and other unbound contaminants in amplification chamber 40 through conduit 34 to plasma waste chamber 36. The bioprobe constituents comprise a magnetic bead 12 which enables the separation of the immunoassay probe 150 for purification and analysis of cells, proteins, DNA, RNA and other molecules. These magnetic beads 12 capture targets of interest such as analyte 10 from the biological samples 28 placed in CD microfluidic 22 and centrifugation steps assist in mixing and concentrating the probe 150. A specific application of this step of conjugating the DNA tag 18 with the antibody 14 of interest, we employ a commercial product such as e.g. Dynabeads, (Thermo Fisher Scientific) where the beads are superparamagnetic particles, meaning that they exhibit magnetic properties when placed in a magnetic field with no residual magnetism once removed from the magnetic field, and their aggregation and primary concentration is achieved by the use of the magnetic array 141. Seethe "Incorporated Disclosure". FIGS. 21A-21F in the Incorporated Disclosure are diagrams showing a sequence for using magnetically actuated nanoparticles in a fluid exchange protocol in both the mixing chamber and SAW chamber. FIG. 22 of the Incorporated Disclosure is a schematic diagram demonstrating the relationship between the three major factors, namely particle size, particle concentration and magnetization, that influence the performance of magnetic nanoparticles in the microfluid disk as used in transfer functions, concentration and magnetophoresis.

Figure 7:
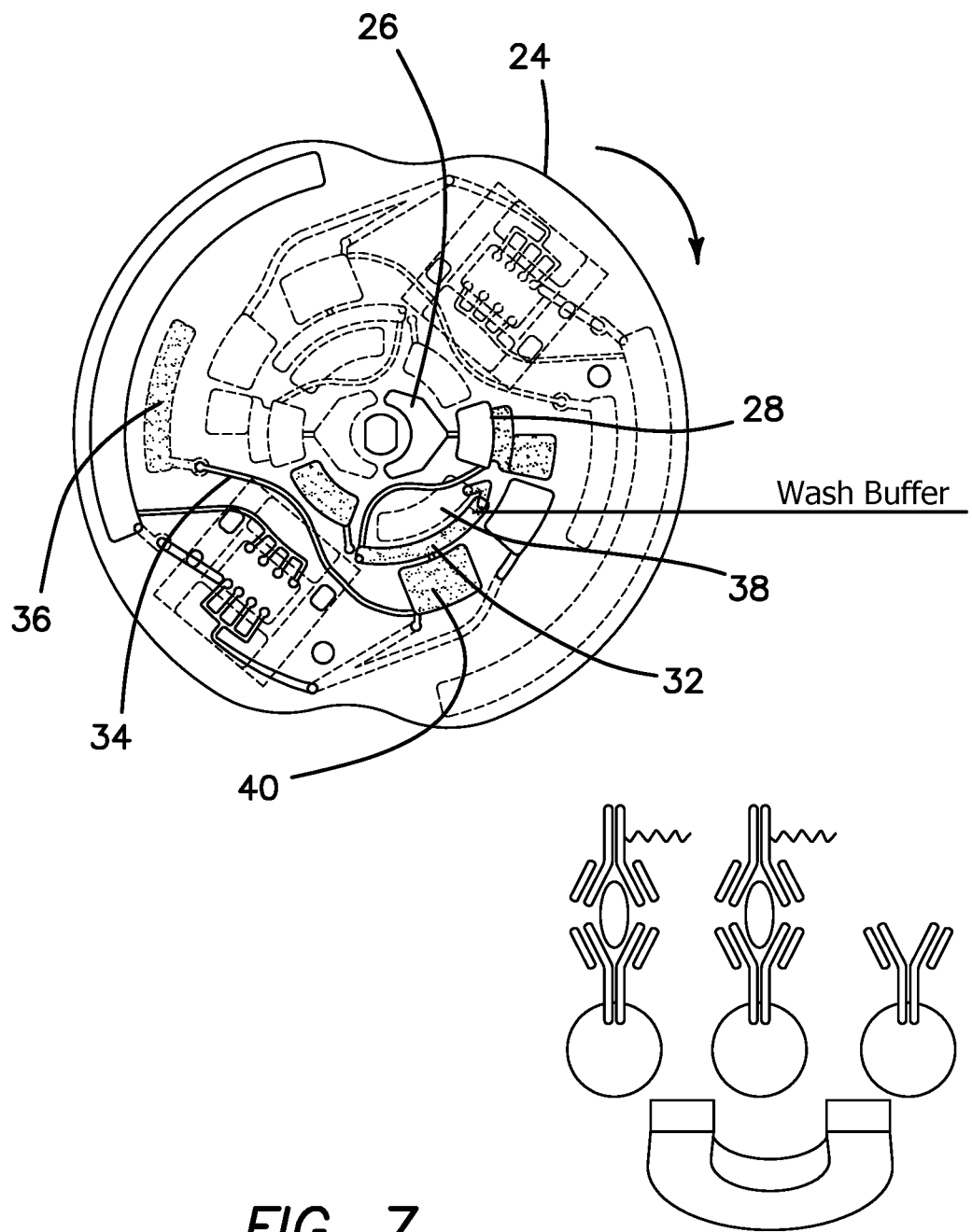
FIG. 7 is a top view diagram of a sixth step in the method of the illustrated embodiment, namely washing away any remaining unbound contaminants.

FIG. 7 is a top view diagram of a sixth step in the method of the illustrated embodiment, namely washing away any remaining unbound contaminants. The magnet fixing antibody-MNP-analyte-antibody-DNA tag complexes 12, 14, 10, 16, 18 remains active so that these complexes are retained in amplification chamber 40. A wash buffer is stored in wash storage chamber 38. Disc 24 is rotated to fill and wash amplification chamber 40 to remove any remaining unbound contaminants and transport them into waste chamber 36. Only bound complexes are left in chamber 40.

FIG. 8 is a top view diagram of a seventh step in the method of the illustrated embodiment, namely resuspension of the antibody—analyte-antibody-DNA tag complexes 12, 14, 10, 16, 18 in an amplification buffer in amplification chamber 40. Storage chamber 42 includes a buffer with primers 44, base pairs 46 and polymerase 48 used to resuspend the antibody-MNP-analyte-antibody-DNA tag complexes 12, 14, 10, 16, 18 in preparation of the isothermal amplification step. Programmed rotation of disc 24 transports the loaded amplification buffer through mixing chamber 32 into amplification chamber 40.

Figure 9:
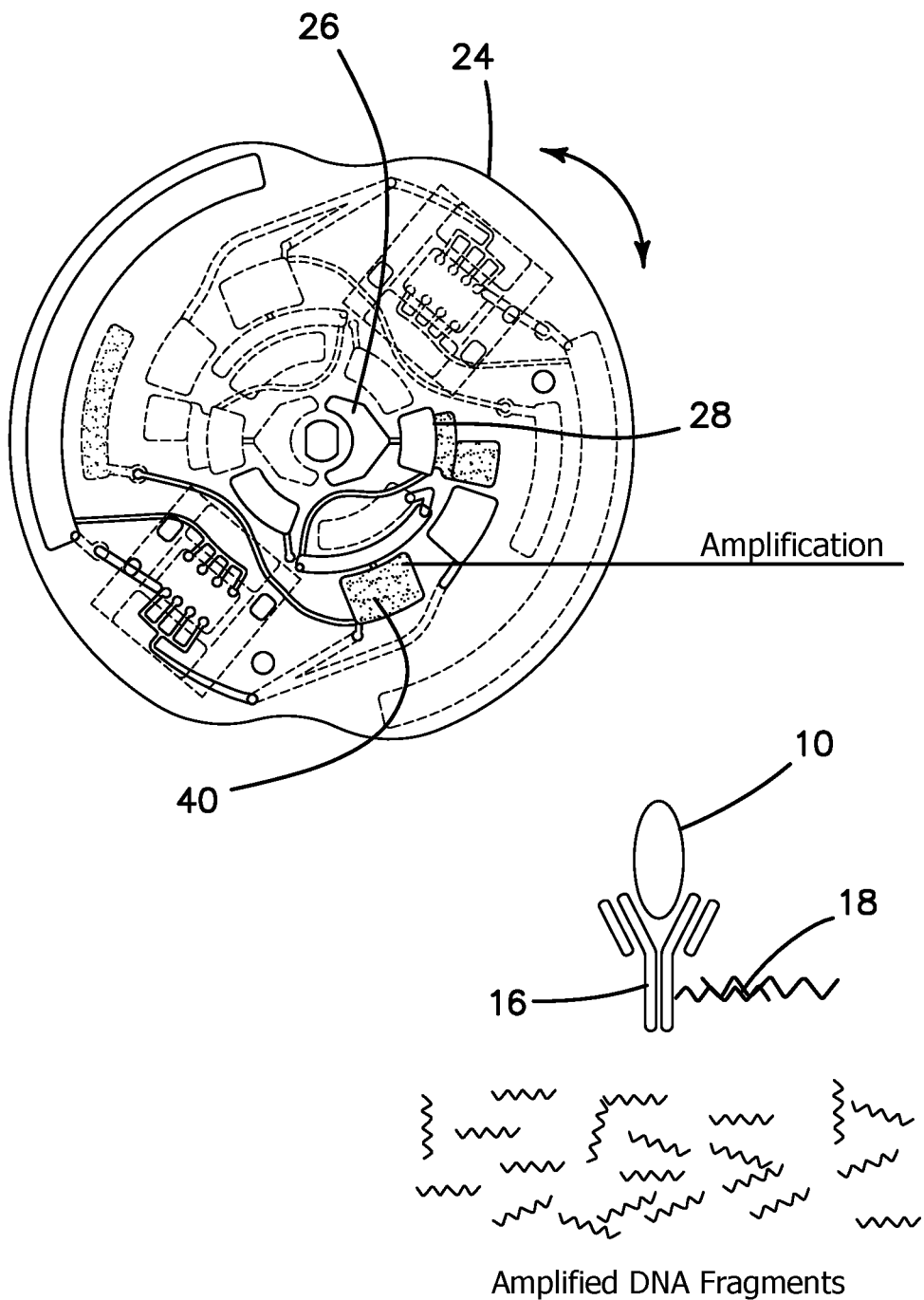
FIG. 9 is a top view diagram of an eighth step in the method of the illustrated embodiment, namely isothermal amplification of the DNA tag.

FIG. 9 is a top view diagram of an eighth step in the method of the illustrated embodiment, namely isothermal amplification of the DNA tag 18. A Peltier element (not shown) in thermal communication with chamber 40 is activated to keep the contents of chamber 40 at 65° C. Disc 24 is held stationary above the Peltier element for a predetermined time, e.g. 10 min to 30 min, which in the case of troponin is about 10 minutes, to allow for sufficient replication of DNA tag 18. What results in the illustrated embodiment is a replication of DNA tag 18 by a factor of about $10^9$ to create free floating DNA tags 20, which are replicas. In the proposed immunoassay complex, we design by fiat a DNA sequence with its primer in such a manner so as to provide a unique sequence. For example, we incorporate a DNA tag 18 whose sequence is borrowed from a DNA tag of C. Elegance and a unique matching sequence primer which is a short nucleic acid sequence that provides a starting point for DNA synthesis. In C. Elegance organisms, primers are short strands of RNA. A primer must be synthesized by an enzyme called primase, which is a type of RNA polymerase, before DNA replication can occur and therefor by employing a DNA tag with unique sequence not found in the human blood, we enable additional specificity to the tag and thereby provide additional screening modality for the purpose of reducing false positive cases of identification. Such a unique DNA tag with its unique primer undergo replications at a statistically significant higher rate than other potential DNA segments which were not eliminated during the wash cycle.

The synthesis of a primer is necessary because the enzymes that synthesize DNA, which are called DNA polymerases, can only attach new DNA nucleotides to an existing strand of nucleotides. The primer therefore serves to prime and lay a foundation for DNA synthesis. The primers are removed before DNA replication is complete, and the gaps in the sequence are filled in with DNA by DNA polymerases. In our application, we design and synthesize DNA primers with specific sequences that bind to sequences in a single-stranded DNA molecule to meet the replication of the unique DNA tag sequence.

In this application where the inherent sensitivity of the SH SAW to mass and viscosity changes is limited by the lowest SNR floor, the use of mass amplification of a DNA tag, demonstrates a method in which the $S_m^\varphi$ is no longer the limiting factor which defines the minimum mass loading at which the sensor and its detector can generate an electrical output proportional to the concentration of the analyte and which defines the resolution of the sensor's output for measuring a minimum mass above the SNR floor.

Figure 10:
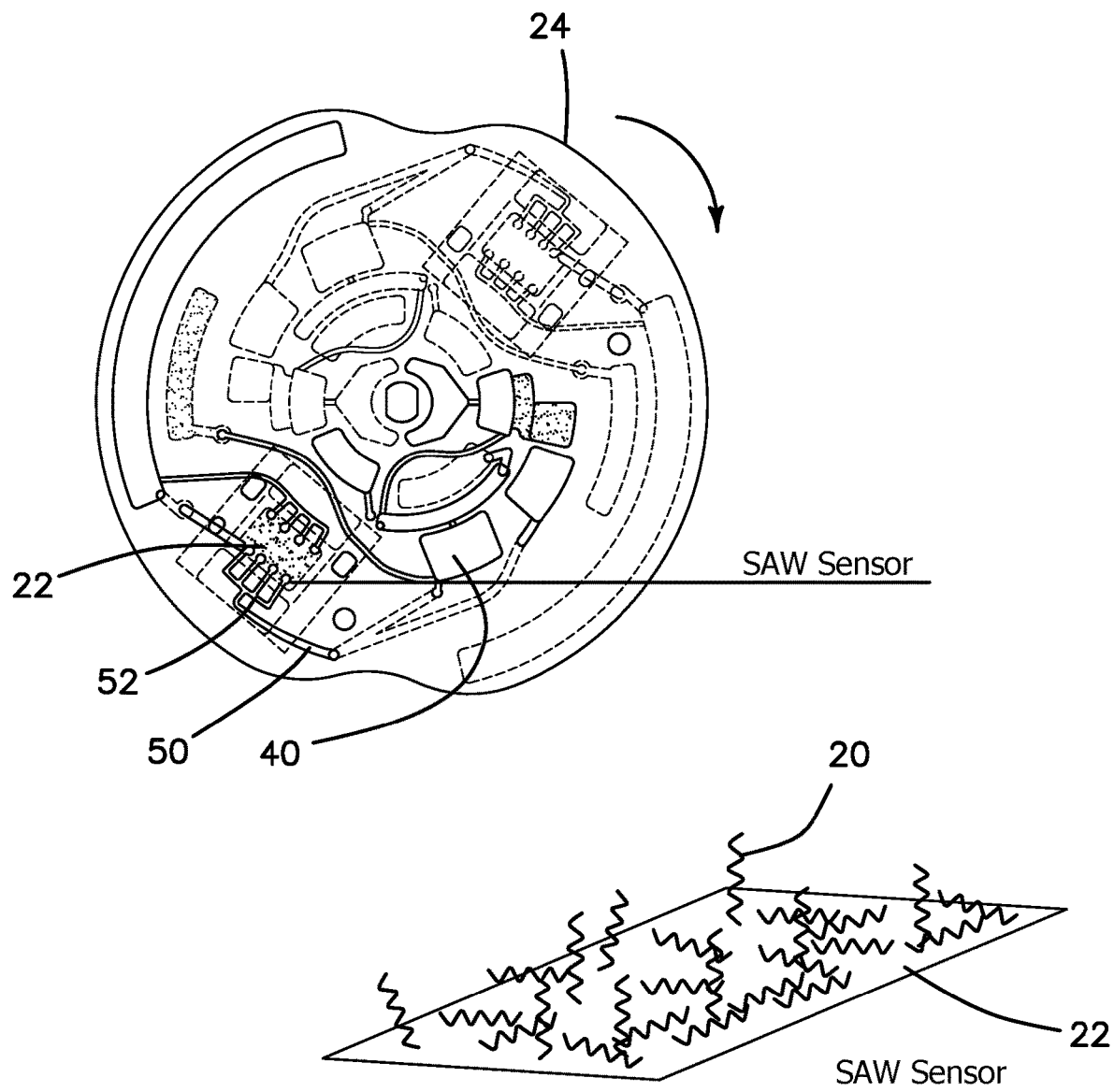
FIG. 10 is a top view diagram of a ninth step in the method of the illustrated embodiment, namely transfer of the replicated free-floating DNA tags to the SAW sensor surface.

FIG. 10 is a top view diagram of a ninth step in the method of the illustrated embodiment, namely transfer of the replicated free-floating DNA tags 20 to the sensor surface of SAW 22. The magnet optionally continues to fix antibody-MNP-analyte-antibody-DNA tag complexes 12, 14, 10, 16, 18 in amplification chamber 40. Disc 24 is rotated for a predetermined time, e.g. 20 s to 40 s, and at a predetermined rate, e.g. 2000 rpm to 4000 rpm, to transport the replicated DNA tags 20 through conduit 50 and distributing manifold 52 into SAW 22, where they settle down onto the sensor surface, where they self-attach. Attachment of DNA tags 20 to sensor surface of SAW 22 is facilitated by coating the sensor surface of SAW 22 with a DNA dye, such as 4', 6-diamindino-2-phenylindole (DAPI), which preferentially binds to double stranded DNA to adenine-thymine rich regions, but not to single stranded DNA or other proteins. The desired DNA tags 20 are double stranded.

Figure 11:
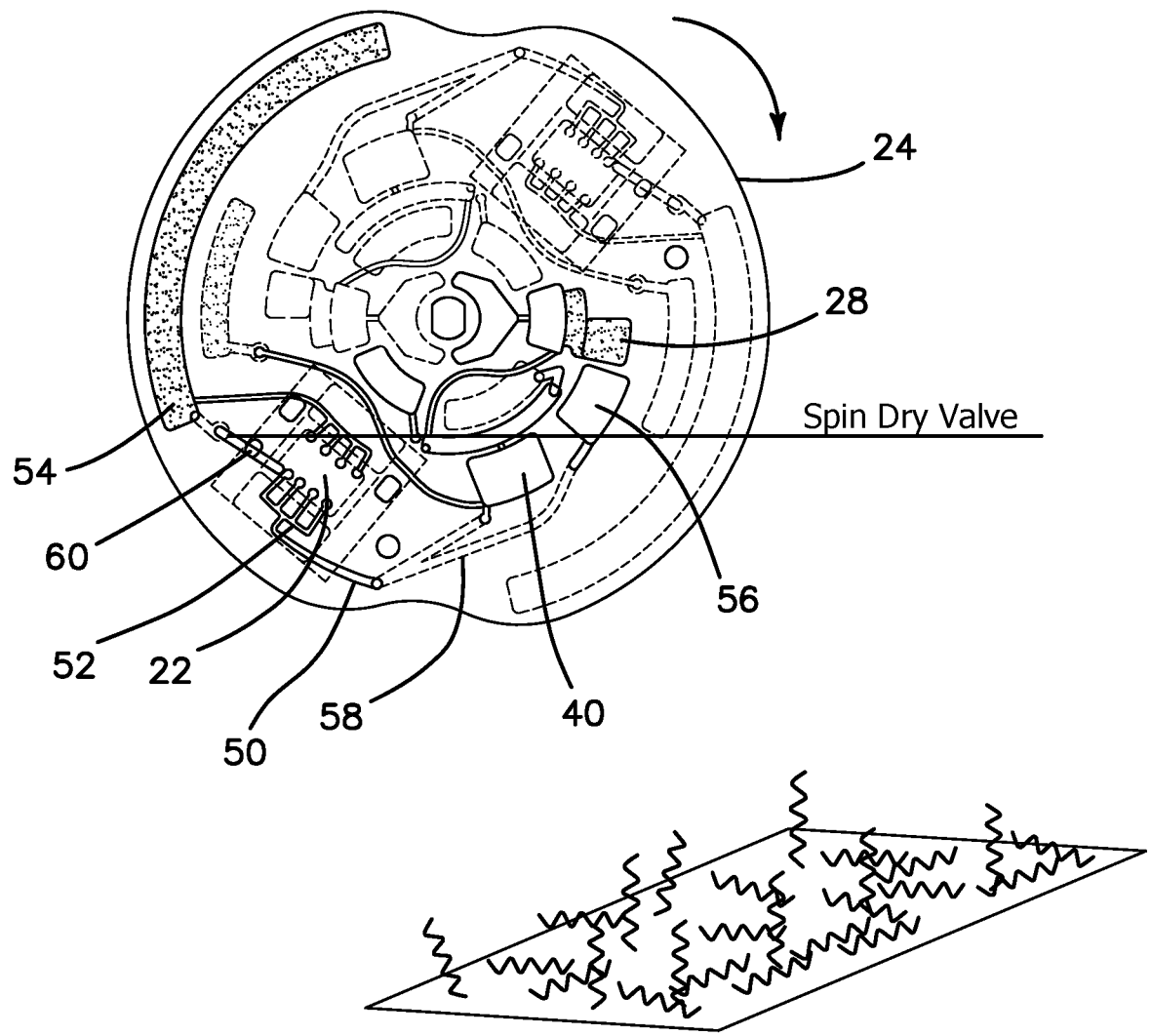
FIG. 11 is a top view diagram of a tenth step in the method of the illustrated embodiment, namely an optional wash and spin dry step.

FIG. 11 is a top view diagram of a tenth step in the method of the illustrated embodiment, namely an optional wash and spin dry step. The method up through FIG. 10 could result in a measurement in SAW 22 is what is termed as wet-wet scheme, where both the mass and viscosity of the DNA tags are used for the measurement, because the SAW measurement is made with the measured DNA tags 20 in a wet environment. In FIG. 11 disc 24 is rotated for a predetermined time, e.g. 20 s to 60 s, and at a predetermined rate, e.g. 2000 rpm to 4000 rpm, to optionally wash and remove fluid and unbound contaminants from SAW 22 using a buffer wash stored in storage chamber 56, transported through conduits 58, 50, manifold 52, SAW 22 and into waste chamber 54. Finally, a valve is opened in conduit 60 using a solid state laser. The disc 24 is then rotated for a predetermined time, e.g. 20 s to 120 s, and at a predetermined rate, e.g. 3000 rpm to 5000 rpm and the remaining wash buffer is transported through conduit 60 into waste chamber 54, allowing all liquid to leave the SAW 22. This results in a measurement in SAW 22 in what is termed as wet-dry scheme, because the SAW measurement is made with the measured DNA tags 20 in a dry environment to ensure that the measured signal is only from the amplified DNA tags 20 and primarily coming from the mass of the DNA tags, to obtain an enhanced output signal undamped by fluid in SAW 22.

Figure 12:
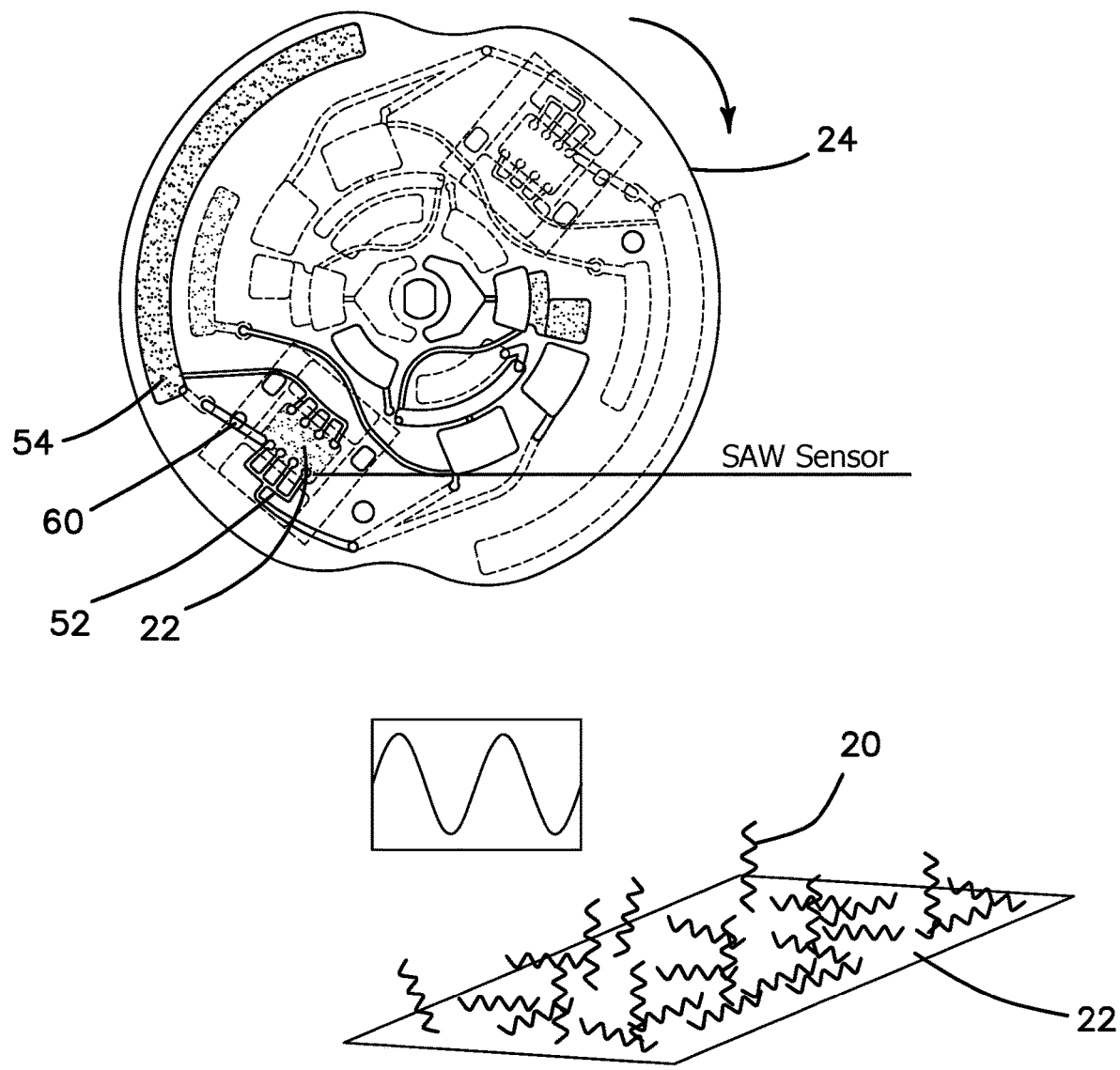
FIG. 12 is a top view diagram of an eleventh step in the method of the illustrated embodiment, namely SAW measurement.

FIG. 12 is a top view diagram of an eleventh step in the method of the illustrated embodiment, namely SAW measurement. An RF signal is applied to SAW 22 and the output SAW signal, a phase shift, is correlated to the amount of analyte 10 captured and its concentration in the sample. Given the amplification or doubling time, the derived concentration measurement is then transmitted to a remote data receiver or to the cloud by the microfluidic reader 62 as described in the Incorporated Disclosure. As a result, laboratory quality assays can be realized in a battery powered, field portable microfluidic reader 62 by a minimally trained operator, utilizing a microfluidic reader 62 as shown in the Incorporated Disclosure, which has been designed or modified as shown above to facilitate practice of the method disclosed above.

Figure 13:
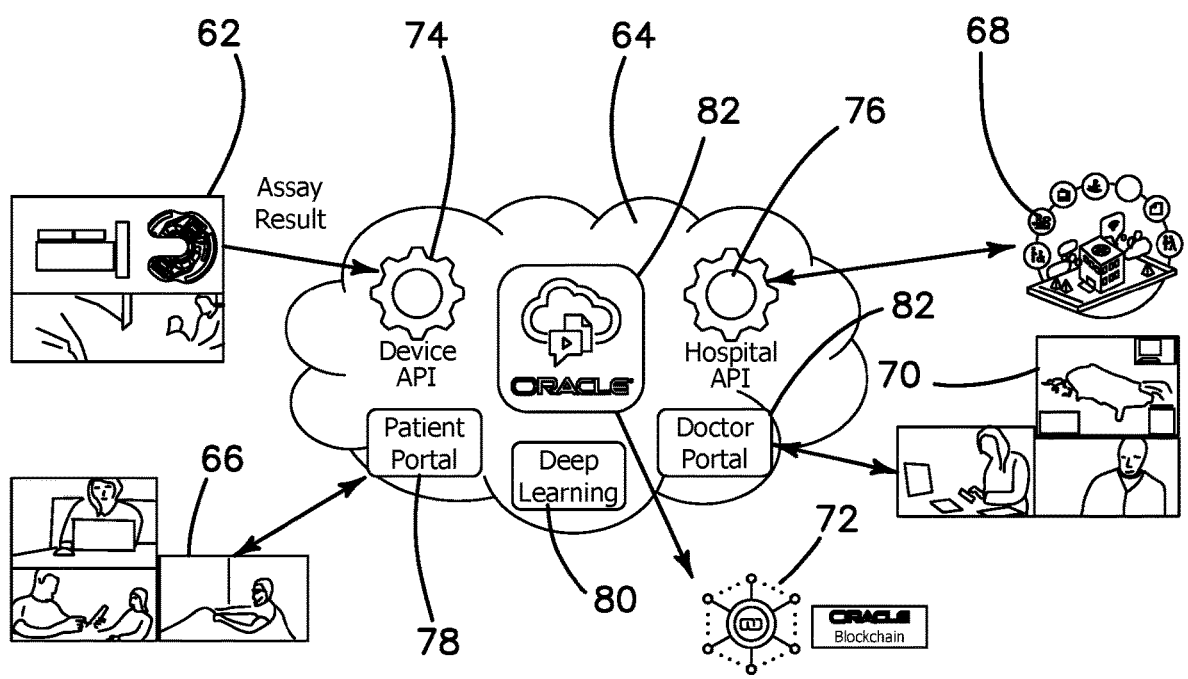
FIG. 13 is a diagram of an interconnected handheld platform computer system comprised of a plurality of electronic modules connected to the cloud and including the disclosed microfluidic reader.

The method described in connection with FIGS. 1-11 must be understood as being performed in a much larger and more sophisticated interconnected computer system such as diagrammatically shown in FIG. 13. The disclosed embodiment of microfluidic reader 62 is communicated to cloud 64 through a reader application programming interface (API)

74 using an encrypted secure link, which allows it to be communicated to patient portals 78, communicated to patients' or user computer systems 66, hospital or clinic computer systems 68 through hospital API 76, doctors' portal 82 communicated to physician's computer systems 70, and deep learning computer systems 80. Reader API 74 is a platform that incorporates the best practices for security, resiliency and reliability of data communication. Deep learning computer systems 80 (also known as deep structured learning or hierarchical learning) are part of a broader family of machine learning methods based on artificial neural networks. Learning can be supervised, semi-supervised or unsupervised. Deep learning architectures such as deep neural networks, deep belief networks, recurrent neural networks and convolutional neural networks have been applied to fields including computer vision, speech recognition, natural language processing, audio recognition, social network filtering, machine translation, bioinformatics, drug design, medical image analysis, material inspection and board game programs, where they have produced results comparable to and in some cases superior to human experts. In this embodiment deep learning medical diagnostic systems are communicated with the results of reader 62 to deep learning computer systems 80 to provide physician's systems 70 with computer assisted diagnosis and therapies. In addition, cloud 64 is managed by one or more cloud server systems 82, which may in turn manage distributed ledger technology (DLT) systems or global block chain computer database systems 72 for storage and maintenance of encrypted databases. The cloud service of FIG. 13 allows for permissioned access to the test results reported by reader 62 from hospitals, doctors and the patients themselves.

Figure 14:
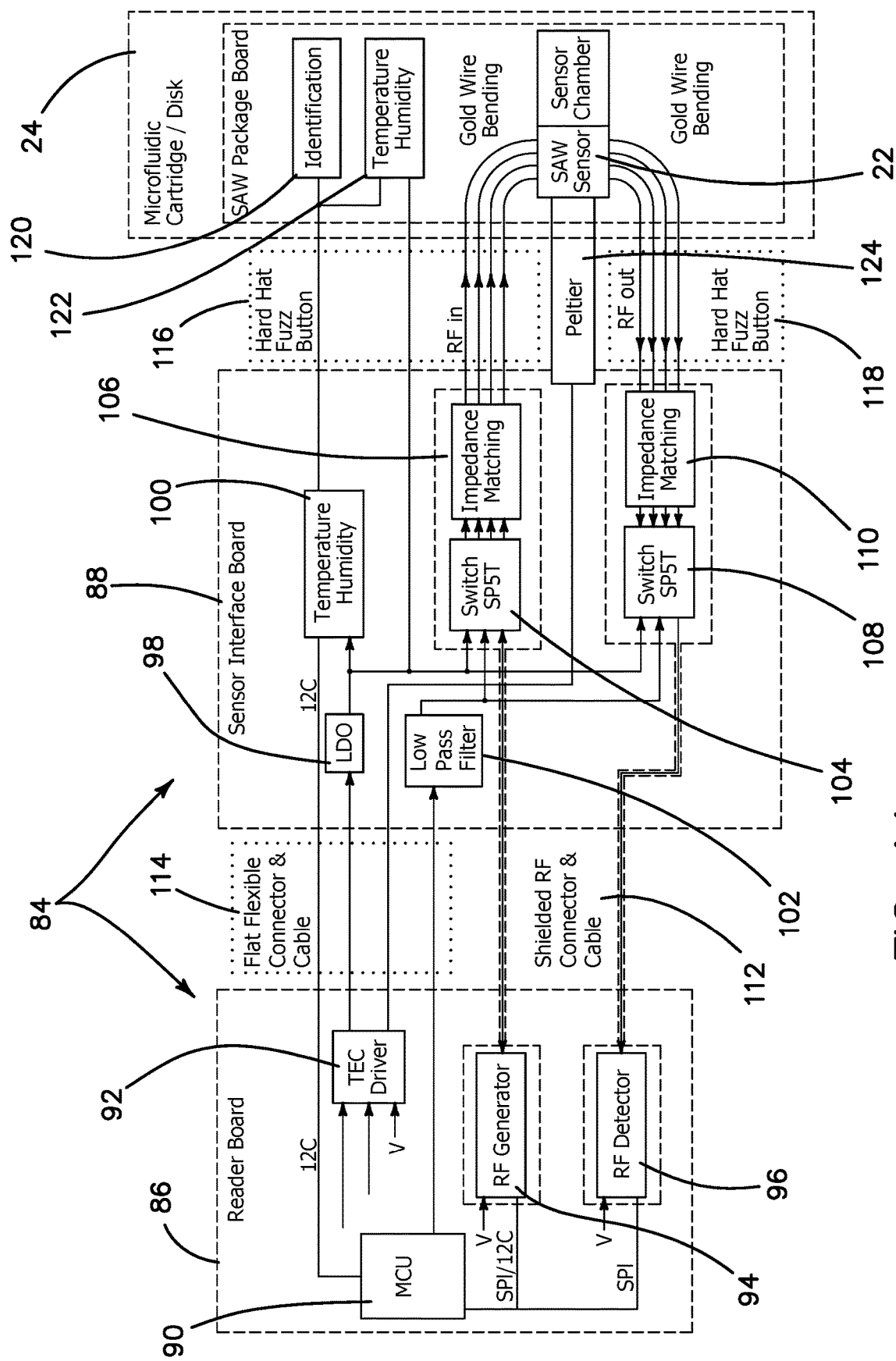
FIG. 14 is a high-level block diagram of the additional elements included in the programmable computer system in addition to those elements described in the Incorporated Disclosure in one embodiment of the reader to operate the microfluidic disc using isothermal amplification.

FIG. 14 is a high-level block diagram of the additional elements included in the programmable computer system 84, in addition to those elements described in the Incorporated Disclosure, in one embodiment of the reader 62 to operate the microfluidic disc 24 using isothermal amplification. System 84 includes a reader board 86 communicated to sensor interface board 88, which in turn is communicated to disc 24. Reader board 86 includes a microcontroller (MCU) 90 coupled to RF generator 94 ultimately coupled to SAW 22 and to an RF detector 96 for receiving an RF output signal from SAW 22, whereby the phase shift resulting from bound DNA tags 20 are ultimately weighed or measured. The RF signals from RF generator 94 and to RF detector 96 are coupled to sensor interface board 88 through a shielded RF connector and cable 112. RF generator 94 is coupled to a single pole-5 throw switch 104 and thence to an impedance matching circuit 106. The output of impedance matching circuit 106 is coupled to SAW 22 through a hard hat fuzz button RF connector 116 into the input of SAW 22. The output of SAW 22 is coupled through a hard hat fuzz button RF connector 118 into an impedance matching circuit 110 and thence to a a single pole-5 throw switch 108. Single pole-5 throw switch 108 is coupled to RF detector 96 through shielded RF connector and cable 112. Switches 104 and 108 are controlled by MCU 90 coupled through flat flexible connector and cable 114 to low pass filter 102 and thence to switches 104, 108.

Because of the use of isothermal amplification, temperature and humidity of the environment of reader 62 are relevant to accurate operation and readings. Low dropout regulator (LDO) 98, drawing its power from reader board 86, is a DC linear voltage regulator that regulates its output voltage even when the supply voltage is very close to the output voltage. LDO 98 supplies switches 104, 108, temperature and humidity controller 100 and temperature and humidity sensor 122. Temperature and humidity controller 100 in turn is coupled through hard hat fuzz button connector 116 to disc identification circuit 120 and temperature and humidity sensors 122 in disc 24. Each disc 24 carries a bar code or other embedded data identifying the disc 24 and/or the type of assay to which the disc 24 is directed to allow the reader 62 to programmable adapt operation and/or reporting to the type of assay being performed. In addition, control or operation of the disc is conditioned and controlled according to the ambient temperature and humidity in which reader 62 is being operated at the time of measurement and assay. Since the biological sample processing, DNA amplification, and SAW sensor reading are highly effected by temperature and humidity, the temperature and humidity sensors, along with the heating/cooling thermoelectric elements on the board, serve to create an environmentally controlled chamber, making sure that critical steps are done at proper temperature and humidity despite adverse or extreme ambient conditions.

Thermoelectric (TEC) driver 92, drawing its power from board 86 and controlled by a pulse width modulated (PWM) signal on board 86, is coupled via cable 114 to Peltier cooler/heater 124, which is thermally coupled to the microfluidic disk to allow for temperature control.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method of assaying an analyte in a sample in a portable, handheld microfluidic reader having a detector with a minimal mass sensitivity limitation comprising:
    providing a portable, handheld microfluidic reader for assaying an analyte in a sample, the reader having a rotatable microfluidic disc, the reader comprising:
        a sample inlet defined in the disc into which the sample is inserted;
        a mixing chamber defined in the disc and selectively communicated to the sample inlet and provided with a first antibody for capturing the analyte having a DNA tag attached thereto;
        an amplification chamber defined in the disc selectively communicated to the mixing chamber provided with a second antibody for capturing the analyte attached to a surface or having a magnetic nanoparticle (MNP) or nanoparticle (NP) attached thereto, where a sandwich including the surface or MNP or NP, first and second antibodies, the analyte and the DNA tag are formed in the amplification chamber; and for replicating the DNA tag using isothermal amplification to produce a predetermined amount of DNA tags; and
        a detector selectively communicated to the amplification chamber and provided in the disc for measuring the amount of replicated DNA tags;
    inserting the sample into the sample inlet;
    capturing the analyte with the first antibody having a DNA tag attached thereto and with the second antibody having an attached magnetic nanoparticle (MNP) or nanoparticle (NP), where the sandwich is formed including the first and second antibodies, the analyte, the MNP, the NP, and the DNA tag;
    replicating the DNA tag using isothermal amplification to the predetermined amount of DNA tags sufficient to overcome the minimal mass sensitivity limitation of the detector by providing an amount is reliably detectable by the detector; and
    measuring the amount of replicated DNA tags using the detector.

2. The method of claim 1 where the sample is a blood sample, where inserting the sample in the reader comprises inserting the blood sample into the sample inlet on the microfluidic rotatable disc, and further comprising moving the blood sample into a blood plasma separation chamber in the microfluidic rotatable disc, and separating the blood into a plasma component including the analyte and a cellular component.

3. The method of claim 2 where capturing the analyte in the blood sample with the first antibody having the DNA tag attached thereto comprises moving the plasma component including the analyte into the mixing chamber on the rotatable disc, mixing the analyte with the first antibody, and binding the analyte to the first antibody.

4. The method of claim 3 further comprising preloading the mixing chamber with the first antibody having the DNA tag attached thereto prior to moving the plasma component including the analyte into the mixing chamber on the rotatable disc.

5. The method of claim 2 where capturing the analyte in the blood sample with the second antibody either attached to the surface or having the MNP or NP attached thereto comprises moving the plasma component including the analyte into the amplification chamber on the rotatable disc, mixing the analyte with the second antibody, and binding the analyte to the second antibody.

6. The method of claim 5 further comprising preloading the amplification chamber with the second antibody attached to the surface of the amplification chamber or having the MNP or NP attached thereto prior to moving the plasma component including the analyte into the amplification chamber on the rotatable disc.

7. The method of claim 1 where capturing the analyte with the first antibody having a DNA tag attached thereto is performed before capturing the analyte in the sample with a second antibody attached to the surface or having the magnetic nanoparticle (MNP) or the nanoparticle (NP) attached thereto.

8. The method of claim 1 where capturing the analyte with the second antibody attached to the surface or having the MNP or NP attached thereto is performed before capturing the analyte in the sample with the first antibody having the DNA tag attached thereto.

9. The method of claim 1 where capturing the analyte with the first antibody having the DNA tag attached and capturing the analyte in the sample with the second antibody attached to the surface or having the magnetic nanoparticle (MNP) or nanoparticle (NP) attached thereto are performed concurrently with each other.

10. The method of claim 1 further comprising fixing the sandwich of the magnetic nanoparticle, first and second antibodies, the analyte and the DNA tag in the amplification chamber by activating a magnetic field extending to the amplification chamber, and removing unbound elements or contaminants from the amplification chamber while leaving the fixed sandwich in the amplification chamber.

11. The method of claim 10 further comprising washing the fixed sandwich in the amplification chamber to flush the amplification chamber and to ensure only captured analyte is retained within the amplification chamber.

12. The method of claim 1 where replicating the DNA tag using isothermal amplification to the predetermined amount detectable by the detector comprises resuspending the sandwich in the amplification chamber in the rotatable disc in a buffer at a constant temperature including primers, base pairs and polymerase for a predetermined time to replicate the DNA tag.

13. The method of claim 12 further comprising maintaining the constant temperature in both the amplification chamber of the disc with the resuspended sandwich therein and a SAW sensor chamber of the disc with the DNA strands attached therein using a Peltier heater/cooler.

14. The method of claim 1 where the detector is a surface acoustic wave (SAW) detector in the disc and further comprising moving the replicated DNA tags from the amplification chamber into the SAW detector and fixing the replicated DNA tags to a sensor surface of the SAW detector.

15. The method of claim 14 further comprising removing unbound elements or contaminants from the sensor surface of the detector and spin drying the sensor surface of the SAW detector by rotating the disc.

16. The method of claim 1 where replicating the DNA tag using isothermal amplification to the predetermined amount of DNA tags detectable by the detector comprises controlling the time during which replication of the DNA tag is allowed, moving the replicated DNA tags from the amplification chamber into the detector and fixing the replicated DNA tags within the detector.

17. The method of claim 16 further comprising determining the amount of analyte in the sample from the amount of time allowed for replication and the measured amount of replicated DNA tags.

18. A portable, handheld microfluidic reader for assaying an analyte in a sample, the reader having a rotatable microfluidic disc, the reader comprising:

a sample inlet defined in the disc into which the sample is inserted;

a mixing chamber defined in the disc and selectively communicated to the sample inlet and provided with a first antibody for capturing the analyte having a DNA tag attached thereto;

an amplification chamber defined in the disc selectively communicated to the mixing chamber provided with a second antibody for capturing the analyte attached to a surface or having a magnetic nanoparticle (MNP) or nanoparticle (NP) attached thereto, where a sandwich including the surface or MNP or NP, first and second antibodies, the analyte and the DNA tag are formed in the amplification chamber; and for replicating the DNA tag using isothermal amplification to produce a predetermined amount of DNA tags; and a detector selectively communicated to the amplification chamber and provided in the disc for measuring the amount of replicated DNA tags.

19. The portable, handheld microfluidic reader of claim 18 where the detector is a surface wave acoustic (SAW) detector.

20. The portable, handheld microfluidic reader of claim 18 where the sample is a blood sample and further comprising a plasma-blood separating chamber having an inlet communicated to the sample inlet and an outlet for communicating plasma including the analyte to the mixing chamber.

* * * * *